United States Patent
Kimishima et al.

(10) Patent No.: US 9,891,592 B2
(45) Date of Patent: Feb. 13, 2018

(54) INFORMATION PROCESSING TO IMPROVE SLEEP EFFICIENCY

(75) Inventors: Masato Kimishima, Tokyo (JP); Naoyuki Onoe, Kanagawa (JP); Tatsuhito Sato, Tokyo (JP); Hideyuki Matsunaga, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 696 days.

(21) Appl. No.: 14/111,018

(22) PCT Filed: Apr. 12, 2012

(86) PCT No.: PCT/JP2012/059958
§ 371 (c)(1),
(2), (4) Date: Oct. 10, 2013

(87) PCT Pub. No.: WO2012/144396
PCT Pub. Date: Oct. 26, 2012

(65) Prior Publication Data
US 2014/0058703 A1    Feb. 27, 2014

(30) Foreign Application Priority Data
Apr. 20, 2011    (JP) .................................. 2011-093701

(51) Int. Cl.
*G04F 10/00* (2006.01)
*G06F 19/00* (2011.01)
(Continued)

(52) U.S. Cl.
CPC ............ *G04F 10/00* (2013.01); *A61B 5/4809* (2013.01); *G06F 19/3406* (2013.01);
(Continued)

(58) Field of Classification Search
USPC ......................................................... 702/177
See application file for complete search history.

(56) References Cited

U.S. PATENT DOCUMENTS

| 7,998,079 B2 | 8/2011 | Nagai et al. |
| 8,454,490 B2 | 6/2013 | Sato et al. |
| 2009/0157672 A1* | 6/2009 | Vemuri .................. G09B 19/00 |

FOREIGN PATENT DOCUMENTS

| JP | 9-294731 A | 11/1997 |
| JP | 11-331369 A | 11/1999 |

(Continued)

OTHER PUBLICATIONS

A Preliminary Assessment of Algorithms for Drowsy and Inattentive Driver Detection on the Road, Mar. 1999, 49 pages, http://ntl.bts.gov/lib/17000/17900/17991/PB2001105783.pdf.*

(Continued)

*Primary Examiner* — Tung Lau
(74) *Attorney, Agent, or Firm* — Chip Law Group

(57) ABSTRACT

The present technique relates particularly to an information processing device, an information processing method, and a program which can improve sleep efficiency. The information processing device according to one aspect of the present technique has: an acquisition unit which acquires information which indicates an action schedule of a user; and a first determination unit which determines whether the user needs to wake up or sleep, and determines the degree of necessity of waking up when determining that the user needs to wake up and the degree of necessity of sleeping when determining the user needs to sleep, according to the action schedule of the user. The present technique is applicable to a mobile device such as a mobile telephone, a PDA and a digital camera.

7 Claims, 23 Drawing Sheets

(51) Int. Cl.
*G06Q 10/10* (2012.01)
*G06Q 50/22* (2012.01)
*G09B 7/00* (2006.01)
*A61B 5/00* (2006.01)
*G11B 27/10* (2006.01)

(52) U.S. Cl.
CPC ....... *G06F 19/3481* (2013.01); *G06Q 10/109* (2013.01); *G06Q 50/22* (2013.01); *G09B 7/00* (2013.01); *G11B 27/105* (2013.01)

(56) References Cited

FOREIGN PATENT DOCUMENTS

| | | |
|---|---|---|
| JP | 2005-261737 A | 9/2005 |
| JP | 2006-296940 A | 11/2006 |
| JP | 2007-108081 A | 4/2007 |
| JP | 2007-179239 A | 7/2007 |
| JP | 2007-195664 A | 8/2007 |

OTHER PUBLICATIONS

Device wakes up drivers asleep at the wheel, 9:15AM BST Apr. 12, 2008, 2 pages.*
By Analysis of EEG, Detection of Sleepiness in the Work and Traffic Environment, 2006 European Sleep Research Society, JSR 15 (Suppl. 1), 1-253, p. 16-17.*
Maho Oki et al., "MediAlaram:alarm-type interface integrating various media", Dai 72 Kai (Heisei 22 nen) Zenkoku Taikai Koen Ronbunshu (3) Network Security, Mar. 8, 2010 (Mar. 8, 2010), pp. 3-187 to 3-188.

* cited by examiner

| USE CASE | SCORE |
|---|---|
| 1. WAKE UP IN MORNING | −40 |
| 2. GET OFF AT SPECIFIC STATION | −80 |
| 3. SLEEP EARLY | +60 |
| 4. TAKE NAP | +20 |

FIG. 19

MUSIC DB (INDIVIDUAL)

A

| NAME OF MUSIC | SLEEPINESS SCORE INCREASE/DECREASE VALUE | SLEEP ONSET/WAKEFULNESS INTENSITY |
|---|---|---|
| "A" | −10 | WAKEFULNESS INTENSITY 1 |
| "B" | +50 | SLEEP ONSET INTENSITY 3 |
| . . . | . . . | . . . |

MUSIC DB (LARGE SCALE USERS)

B

| NAME OF MUSIC | SLEEPINESS SCORE INCREASE/DECREASE VALUE | SLEEP ONSET/WAKEFULNESS INTENSITY |
|---|---|---|
| "A" | −35 | WAKEFULNESS INTENSITY 2 |
| "B" | +70 | SLEEP ONSET INTENSITY 4 |
| . . . | . . . | . . . |

FIG. 20

| SLEEPINESS SCORE INCREASE/ DECREASE VALUE | SLEEP ONSET/ WAKEFULNESS INTENSITY |
|---|---|
| ~ -100 | WAKEFULNESS INTENSITY 5 |
| -100 ~ -75 | WAKEFULNESS INTENSITY 4 |
| -75 ~ -50 | WAKEFULNESS INTENSITY 3 |
| -50 ~ -25 | WAKEFULNESS INTENSITY 2 |
| -25 ~ 0 | WAKEFULNESS INTENSITY 1 |
| 0 ~ 25 | SLEEP ONSET INTENSITY 1 |
| 25 ~ 50 | SLEEP ONSET INTENSITY 2 |
| 50 ~ 75 | SLEEP ONSET INTENSITY 3 |
| 75 ~ 100 | SLEEP ONSET INTENSITY 4 |
| 100 ~ | SLEEP ONSET INTENSITY 5 |

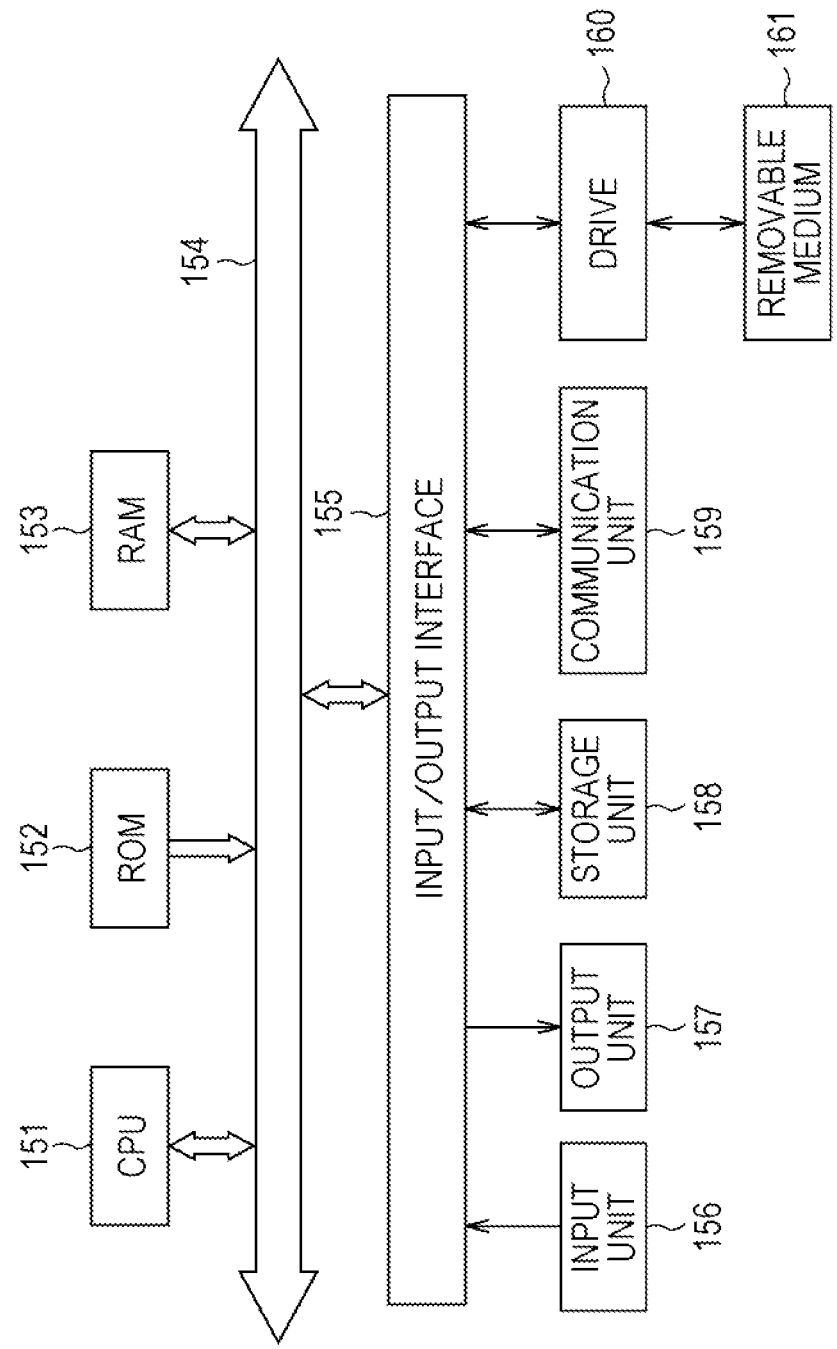

INFORMATION PROCESSING TO IMPROVE SLEEP EFFICIENCY

CROSS-REFERENCE TO RELATED APPLICATION

The present application is a national phase entry under 35 U.S.C. § 371 of International Application No. PCT/JP2012/059958 filed Apr. 12, 2012, published on Oct. 26, 2012 as WO 2012/144396 A1, which claims priority from Japanese Patent Application No. JP 2011-093701 filed in the Japanese Patent Office on Apr. 20, 2011.

TECHNICAL FIELD

The present technique relates particularly to an information processing device, an information processing method, and a program which can improve sleep efficiency.

BACKGROUND ART

Importance of sleep is being recognized. It is known that chronic lack of sleep causes a physical influence such as a decrease in physical strength and a decrease in immune strength, and is likely to cause a metal influence such as depression.

Although people understand the importance of sleep, people cannot secure a sufficient sleep time or have quality sleep due to various situations.

CITATION LIST

Patent Document

Patent Document 1: Japanese Patent Application Laid-Open No. 2007-195664

SUMMARY OF THE INVENTION

Problems to be Solved by the Invention

When a person wakes up from a sleeping state, fulfillment of sleep upon wake-up differ when the person is routed or when the person is woken up slowly. Further, when a person falls asleep from an awake state, fulfillment of sleep differs when the person hardly falls asleep and when the person smoothly falls asleep.

This shows the difference in sleep efficiency depending on a way of sleep onset and a way of arousal even when the sleep time is the same.

The present technique has been made in light of this situation, and the present technique can improve sleep efficiency.

Solutions to Problems

The information processing device according to one aspect of the present technique has: an acquisition unit which acquires information which indicates an action schedule of a user; and a first determination unit which performs at least one of determination as to at least one of whether or not the user needs to wake up and whether or not the user needs to sleep, and determination as to a degree of necessity of waking up when the user needs to wake up and a degree of necessity of sleeping when the user needs to sleep, according to the action schedule of the user.

The first determination unit can calculate a first score which indicates the degree of necessity of waking up or the degree of necessity of sleeping when determining the degree of necessity of waking up or the degree of necessity of sleeping.

A second determination unit which calculates a second score which indicates a degree of sleepiness of the user based on data detected by a sensor can be provided.

A selection unit which selects content to play back based on the first score and the second score, and a playback unit which plays back the content selected by the selection unit can be further provided.

A storage unit which stores, for a plurality of items of content, information which indicates a relationship between the content and a degree of change of sleepiness caused in the user who views the content can be further provided. In this case, the selection unit can select the content which causes the change of the sleepiness corresponding to a difference between the first score and the second score, based on the information stored in the storage unit.

The second determination unit can further calculate the second score based on the data detected by the sensor after the content is played back, and an update unit which updates the information which is stored in the storage unit and which indicates the degree of the change of the sleepiness caused by the content played back, based on a difference between the second score calculated before the content starts being played back and the second score calculated after the content is played back.

A wake-up unit which, when the first determination unit determines that the user needs to wake up and determines the degree of necessity of waking up, wakes up the user according to the degree of necessity of waking up, and a sleep onset unit which, when the first determination unit determines that the user needs to sleep and determines the degree of necessity of sleeping, gets the user to sleep according to the degree of necessity of sleeping can be further provided.

According to one aspect of the present technique, information which indicates an action schedule of a user is acquired, and at least one of determination as to at least one of whether or not the user needs to wake up and whether or not the user needs to sleep, and determination as to a degree of necessity of waking up when the user needs to wake up and a degree of necessity of sleeping when the user needs to sleep, is performed according to the action schedule of the user.

Effects of the Invention

The present technique can improve sleep efficiency.

BRIEF DESCRIPTION OF DRAWINGS

FIG. 19 is a view illustrating an example of a music DB.

FIG. 20 is a view illustrating an example of a correspondence between a sleepiness score increase/decrease value and a sleep onset/wakefulness intensity.

FIG. 26 is a block diagram illustrating an example structure of a computer.

MODES FOR CARRYING OUT THE INVENTION

The following is a description of embodiments for carrying out the present technique. Explanation will be made in the following order.
1. Concept of Improvement of Sleep Efficiency by Information Processing Device
2. Example Structure of Information Processing Device
3. Operation of Information Processing Device
First Embodiment (Example of Comfortable Wake-Up)
Second Embodiment (Example of Prevention of Oversleep on Train)
Third Embodiment (Example of Early Bedding) Fourth Embodiment (Example of Nap)
4. Music Selection/Playback Operation
5. Modified Example 1. Concept of Improvement of Sleep Efficiency by Information Processing Device FIG. 1 is a view illustrating an information processing device according to an embodiment of the present technique.

Figure 1:
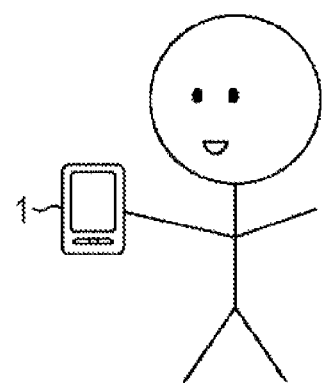
FIG. 1 is a view illustrating an information processing device according to an embodiment of the present technique.

An information processing device 1 in FIG. 1 is a portable device such a mobile telephone, a PDA (Personal Digital Assistants), a digital camera or a PND (Portable Navigation Device), and has a housing of a size which the user can grip by one hand. A display unit formed with a LCD (Liquid Crystal Display) is provided in front of the housing of the information processing device 1.

The information processing device 1 has as an internal memory a schedule DB which is a DB (Data Base) which stores information of an action schedule of a user. The information processing device 1 determines whether the user needs to wake up or sleep now based on the action schedule of the user. The information processing device 1 calculates a wakefulness score which indicates a degree of necessity of waking up by a numerical value when determining that the user needs to wake up, and calculates a sleep onset score which indicates the degree of necessity of sleeping by a numerical value when determining that the user needs to sleep.

Further, the information processing device 1 calculates a sleepiness score which indicates a desire for sleep of the user, that is, sleepiness by a numerical value, based on sensor data detected by various sensors.

The information processing device 1 has a function of playing back music, and selects and plays back music which can cause a change of sleepiness in the user such that the sleepiness score becomes close to the wakefulness score or the sleep onset score. To music which can be played back by the information processing device 1, information which indicates a change of sleepiness caused in the user who listens to this music is set. The information processing device 1 outputs a sound obtained by playing back the music from a speaker of the information processing device 1 or earphones mounted on the information processing device 1 to the user to listen.

When the user is sleeping now and it is determined that the user needs to wake up, the information processing device 1 can set the sleepiness score of the user close to the wakefulness score by selecting and playing back music taking into account the sleepiness score and the wakefulness score of the user.

Further, when the user is sleeping now and it is determined that the user needs to sleep, the information processing device 1 can set the sleepiness score of the user close to the sleep onset score by selecting and playing back music taking into account the sleepiness score and the sleep onset score of the user.

The wakefulness score which indicates the degree of necessity of waking up and the sleep onset score which indicates the degree of necessity of sleeping represent ideal sleepiness scores of the user determined based on an action schedule.

A use case of the information processing device 1 will be described.

[Use Case 1]

Figure 2:
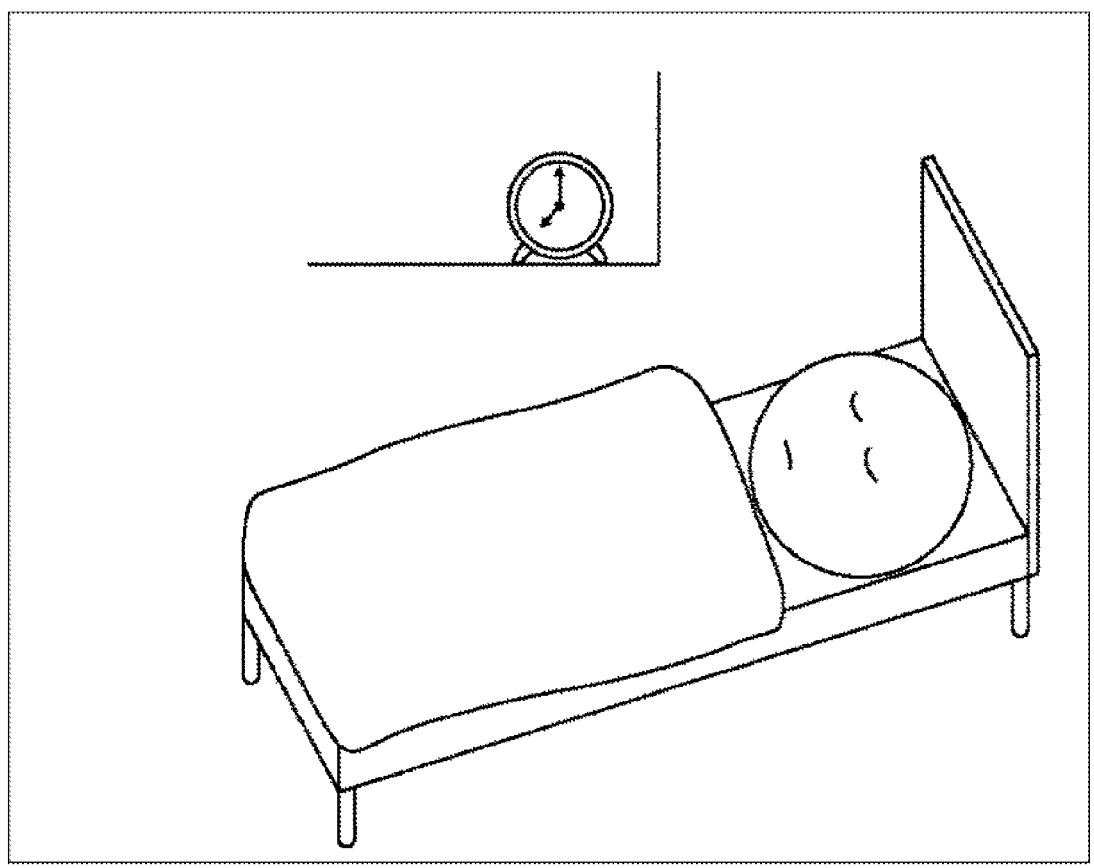
FIG. 2 is a view illustrating a first example of a use case of the information processing device.

FIG. 2 is a view illustrating a first example of a use case of the information processing device 1.

A case will be described where the user is sleeping at home and wakes up in the morning. When determining based on an action schedule of the user that the user needs to wake up since a current time is close to a wake-up time such as 7 o'clock in the morning, the information processing device 1 calculates a wakefulness score which indicates the degree of necessity of waking up. The wake-up time of the user is determined in advance by the information processing device 1 based on, for example, the action history of the user. The wakefulness score calculated in this case is a score lower than a wakefulness score calculated when, for example, it is determined that the user needs to wake up so as not to oversleep on a train as described below.

Further, the information processing device 1 calculates a sleepiness score of the user based on sensor data. The sleepiness calculated in this case is a small score when the sleep time is long and the user already slept sufficiently, and is a high score when the sleep time is short and the user does not sleep much.

The information processing device 1 selects and plays back music which can cause a change of sleepiness in the user such that the sleepiness score becomes close to the wakefulness score. In case of the fixed wakefulness score, when the sleepiness score is high, music which causes a significant change of sleepiness is played back and, when the sleepiness score is low, music which causes a little change of sleepiness is played back.

It is necessary to decrease the sleepiness score to wake up the user. Music which causes a significant change of sleepiness to decrease the sleepiness score is, for example, music of a fast pace, music of a large volume and music including a vocal audio. Further, music which causes a little change of sleepiness to decrease the sleepiness score is, for example, music of a slower pace than music which causes a significant change of sleepiness, music of a small volume and music without a vocal audio.

By this means, when the user already sufficiently slept and sleepiness is a little, the user can comfortably wake up listening to music of a slow pace. The user comfortably wakes up, so that sleep efficiency increases.

[Use Case 2]

Figure 3:
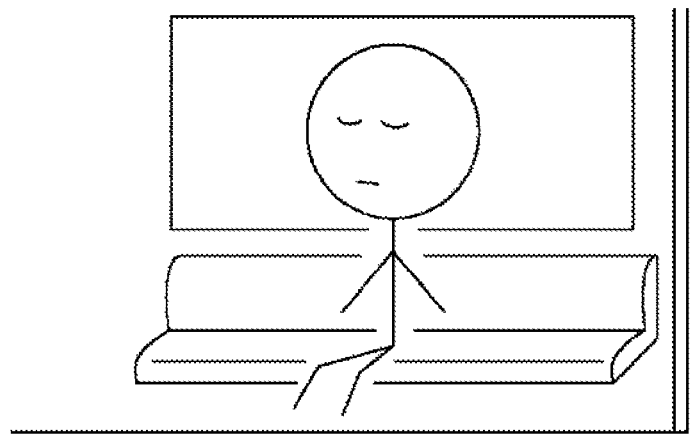
FIG. 3 is a view illustrating a second example of a use case of the information processing device.

FIG. 3 is a view illustrating a second example of a use case of the information processing device 1.

A case will be described where the user is on the train and is sleeping at a seat. When determining based on an action schedule of the user that the user needs to wake up now since the train approaches a get-off station, the information processing device 1 calculates a wakefulness score which indicates the degree of necessity of waking up. Hereinafter, although the get-off station is the nearest station of a house or a company of the user below, the get-off station may be another station.

The nearest station is determined in advance by the information processing device 1 based on, for example, an action history of the user. Further, whether or not the train on which the user is approaches the nearest station is determined by the information processing device 1 based on, for example, a time table of the train. The wakefulness score calculated in this case is a score higher than the wakefulness score calculated in case of use case 1.

Further, the information processing device 1 calculates a sleepiness score of the user based on sensor data. The information processing device 1 selects and plays back music which can cause a change of sleepiness in the user such that the sleepiness score becomes close to the wakefulness score. When the same sleepiness score as that of use case 1 is calculated, the wakefulness score is high, and music which causes a significant sleepiness change compared to use case 1 is played back.

Consequently, the user can listen to music which causes a significant change of sleepiness, so that the user can wake up before the train arrives at the nearest station and be prevented from oversleeping. The user does not need to worry about oversleeping and can safely sleep on the train, so that the sleep efficiency increases.

[Use Case 3]

Figure 4:
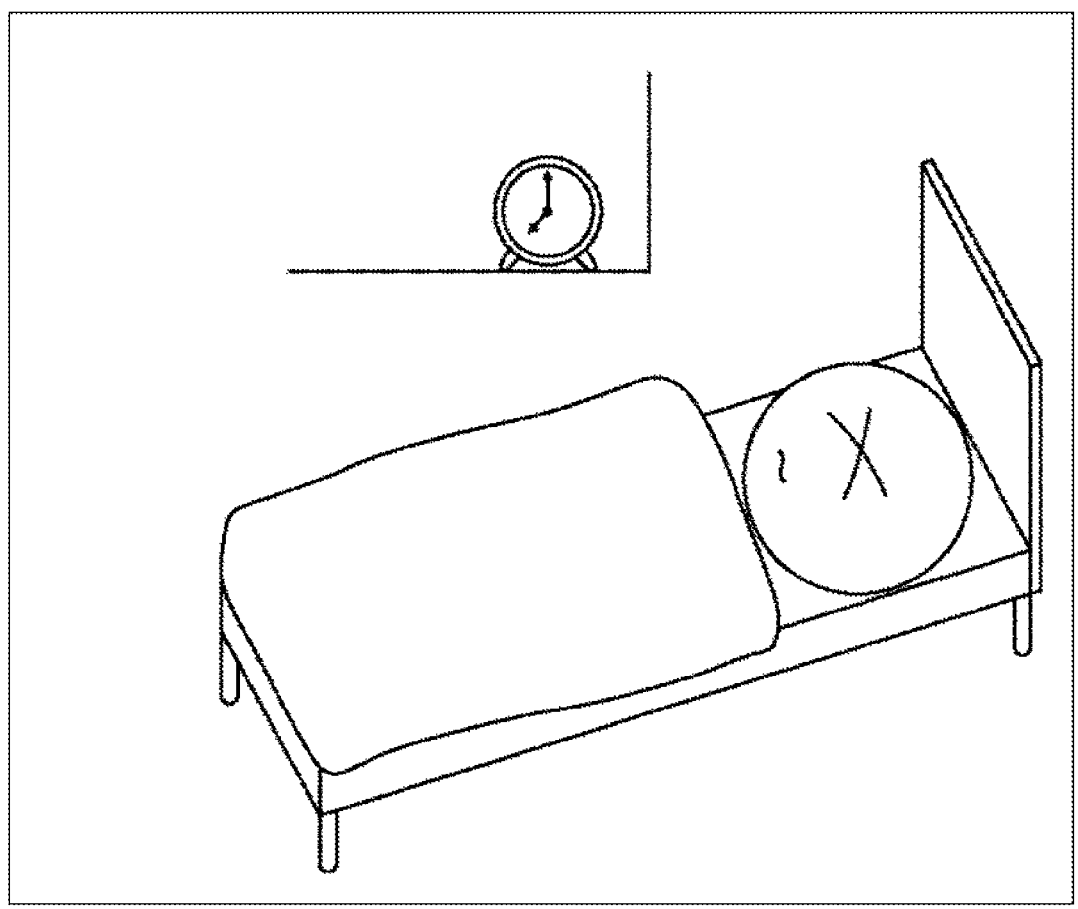
FIG. 4 is a view illustrating a third example of a use case of the information processing device.

FIG. 4 is a view illustrating a third example of a use case of the information processing device 1.

A case will be described where the user needs to wake up early in the next morning and sleeps at an earlier time than usual. When determining that the user needs to sleep based on the action schedule of the user, the information processing device 1 calculates a recommended bedtime. When, for example, the user has a schedule of going out at an earlier time than a usual wake-up time as an action schedule of the next day, the recommended bedtime is determined by the information processing device 1 to recommend a time which is a predetermined time such as eight hours based on a time to go out.

The information processing device 1 calculates a sleepiness score of the user based on sensor data. The sleepiness score calculated in this case is a low score when the current time is a time which is much before a usual bedtime, and is a high score when the current time is a time which is close to the usual bedtime.

Further, the information processing device 1 calculates a sleep onset score which indicates the degree of necessity of sleeping. The information processing device 1 selects and plays back music which can cause a change of sleepiness in the user such that the sleepiness score becomes close to the sleep onset score.

It is necessary to increase the sleepiness score to get the user to sleep. Further, music which causes a little change of sleepiness to increase the sleepiness score is, for example, music of a slow pace, music of a small volume and music without a vocal audio. Further, music which causes a significant change of sleepiness to increase the sleepiness score is, for example, music of a slow pace than music which causes a little change of sleepiness, music of a very small volume and music without a vocal audio.

When the user listens to music which starts being played back at a timing which enables the user to sleep at the recommended bedtime, sleepiness increases, so that the user can sleep at an early time even when the user needs to wake up early in the next morning. The user can smoothly fall asleep compared to a case that the user hardly falls asleep as illustrated in FIG. 4, so that the sleep efficiency increases.

[Use Case 4]

Figures 5, 6:
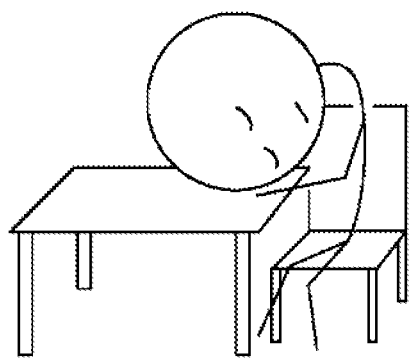
FIG. 5 is a view illustrating a fourth example of a use case of the information processing device.
FIG. 6 is a view illustrating examples of a wakefulness score and a sleep onset score.

FIG. 5 is a view illustrating a fourth example of a use case of the information processing device 1.

A case will be described where, during working hours at a company, the user have a time until the next meeting and takes a nap. When specifying that the user has a time until a start time of the next meeting based on the action schedule of the user, the information processing device 1 determines that the user needs to sleep and calculates the sleep onset score which indicates the degree of necessity of sleeping. The sleep onset score calculated in this case is, for example, a higher score when, for example, an end time of work on a previous day comes later and is a higher score when there is a more time until a start time of the next meeting.

Further, the information processing device 1 calculates a sleepiness score of the user based on sensor data. The information processing device 1 selects and plays back music which can cause a change of sleepiness in the user such that the sleepiness score becomes close to the sleep onset score.

When the current time comes close to the start time of the meeting, an operation of waking up the user is performed by the information processing device 1 similar to use cases 1 and 2.

When the user listens to music, sleepiness increases, so that the user can take a nap at a desk in a company as illustrated in FIG. 5 when there is a time until the next meeting. The user can smoothly fall asleep when there is a time, so that the sleep efficiency increases.

[Specific Example of Score]

FIG. 6 is a view illustrating examples of a wakefulness score and a sleep onset score.

In FIG. 6, scores lower than 0 indicate wakefulness scores, and scores higher than 0 indicate sleep onset scores. The maximum of wakefulness scores is 100 (−100), and the maximum of sleep onset scores is 100.

In case of, for example, use case 1, a wakefulness score is calculated as 40 (−40) to gradually wake up the user. Further, in case of use case 2, a wakefulness score is calculated as 80 (−80) to quickly wake up the user.

In case of use case 3, a sleep onset score is calculated as 60 (−60) to get the user to deeply sleep. Further, in case of use case 4, the user is taking a nap, and therefore the sleep onset score is calculated as 20 (+20).

An operation of the information processing device 1 in each of the above use cases will be described below with reference to the flowcharts.

2. Example Structure of Information Processing Device

Figure 7:
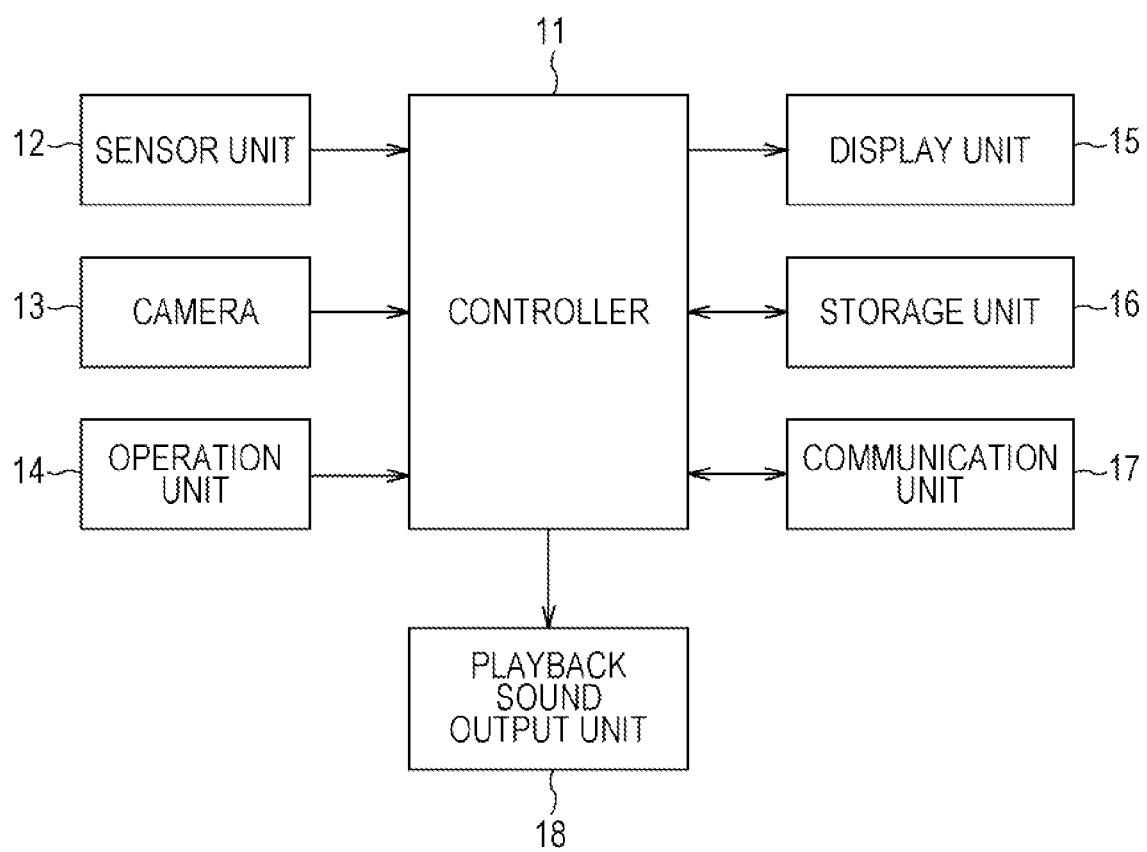
FIG. 7 is a block diagram illustrating a hardware configuration example of the information processing device.

FIG. 7 is a block diagram illustrating a hardware configuration example of the information processing device 1.

The information processing device 1 is formed by connecting a sensor unit 12, a camera 13, an operation unit 14, a display unit 15, a storage unit 16, a communication unit 17 and a playback sound output unit 18 to a controller 11.

The controller 11 has a CPU (Central Processing Unit), a ROM (Read Only Memory) and a RAM (Random Access Memory). The CPU of the controller 11 loads a program from the ROM and executes the program using the RAM to control the entire operation of the information processing device 1.

The sensor unit 12 is formed with various sensors such as a sensor which detects biological information which is information related to a body of the user and a sensor which detects device information which is information related to the information processing device 1. Sensors which detect information related to the body of the user include a pulse sensor which detects a pulse of the user, a body temperature sensor which detects a body temperature and a brain wave sensor which detects a brain wave. Data which indicates the pulse, the body temperature and the brain wave detected by these sensors is outputted to the controller 11.

Meanwhile, sensors which detect information related to the information processing device 1 include an acceleration sensor, a gyro sensor and a GPS (Global Positioning System). Data which indicates an acceleration and an angle detected by these sensors and generated by the information processing device 1, and data which indicates the position of the information processing device 1 are outputted to the controller 11.

The camera 13 includes an image capturing element such as a CMOS (Complementary Metal Oxide Semiconductor) image sensor, and generates image data by performing photoelectric conversion of light taken in by a lens provided on a back surface side of the housing of the information processing device 1. For example, the camera 13 captures an image of the user, and outputs the image of the face to the controller 11.

The operation unit 14 includes, for example, buttons provided on a surface of the housing of the information processing device 1 and a touch panel provided stacked on a display such as a LCD which forms the display unit 15. The operation unit 14 detects a user's operation, and outputs information which indicates content of the detected operation to the controller 11.

The display unit 15 displays various pieces of information such as an image and a text according to control of the controller 11.

The storage unit 16 is formed with a flash memory. The storage unit 16 stores various pieces of information of the schedule DB which is a DB of schedule information which indicates an action schedule of the user and a music DB which is a DB of music.

The communication unit 17 receives a radio wave from a base station, and performs communication with a server on a network such as a LAN (Local Area Network) or the Internet through the network.

The playback sound output unit 18 is formed with a signal processing unit which outputs a signal of music to speakers provided in the information processing device 1 and earphones mounted on an earphone jack of the information processing device 1. The playback sound output unit 18 outputs music played back by the controller 11 for the user to listen.

Figure 8:
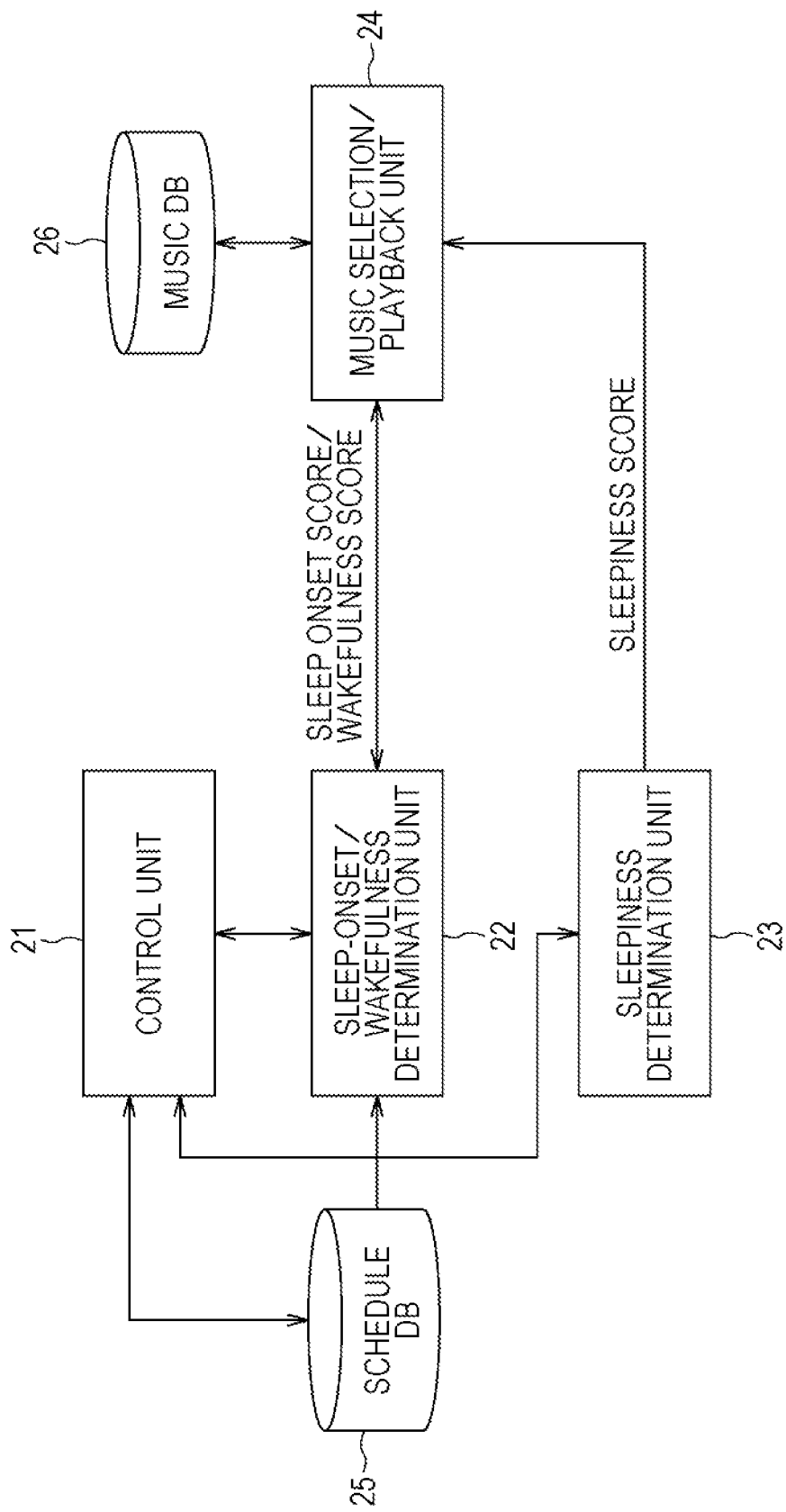
FIG. 8 is a block diagram illustrating a functional configuration example of the information processing device.

FIG. 8 is a block diagram illustrating a functional configuration example of the information processing device 1. At least part of functional units illustrated in FIG. 8 is realized when the controller 11 in FIG. 7 executes a predetermined program.

In the information processing device 1, a control unit 21, a sleep onset/wakefulness determination unit 22, a sleepiness determination unit 23, a music selection/playback unit 24, a schedule DB 25 and a music DB 26.

The control unit 21 learns a user's action based on sensor data supplied from the sensor unit 12, and specifies a wake-up time and the nearest station of the user. The control unit 21 registers information of the specified wake-up time and nearest station in the schedule DB 25. Further, the control unit 21 controls the sleep onset/wakefulness determination unit 22 to calculate a wakefulness score or a sleep onset score, and controls the sleepiness determination unit 23 to calculate a sleepiness score.

The sleep onset/wakefulness determination unit 22 reads schedule information from the schedule DB 25, and determines whether the user needs to wake up or sleep, based on an action schedule of the user. The schedule DB 25 includes a DB which stores business operation related (work related) schedule information of the user and a DB which stores personal life related schedule information.

The sleep onset/wakefulness determination unit 22 calculates a wakefulness score when determining that the user needs to wake up, and calculates a sleep onset score when determining that the user needs to sleep. The sleep onset/wakefulness determination unit 22 outputs the calculated wakefulness score or sleep onset score to the music selection/playback unit 24.

The sleepiness determination unit 23 calculates a sleepiness score based on the sensor data supplied from the sensor unit 12. The sleepiness determination unit 23 outputs the calculated sleepiness score to the music selection/playback unit 24.

The music selection/playback unit 24 selects and plays back music based on the wakefulness score or the sleep onset score calculated by the sleep onset/wakefulness determination unit 22 and the sleepiness score calculated by the sleepiness determination unit 23. The music selection/playback unit 24 selects music targeting at music stored in the music DB 26.

The music DB 26 stores a plurality of items of music data. Music data is taken in the information processing device 1 by the user in advance. To each music the data of which is stored in the music DB 26, information which indicates a change of sleepiness caused in the user who listens to this music is set as meta data.

In addition, the schedule DB 25 and the music DB 26 can be realized on the server on the network. In this case, data is transmitted and received between the schedule DB 25, the music DB 26 and each unit in FIG. 8 through the communication unit 17.

Figure 9:
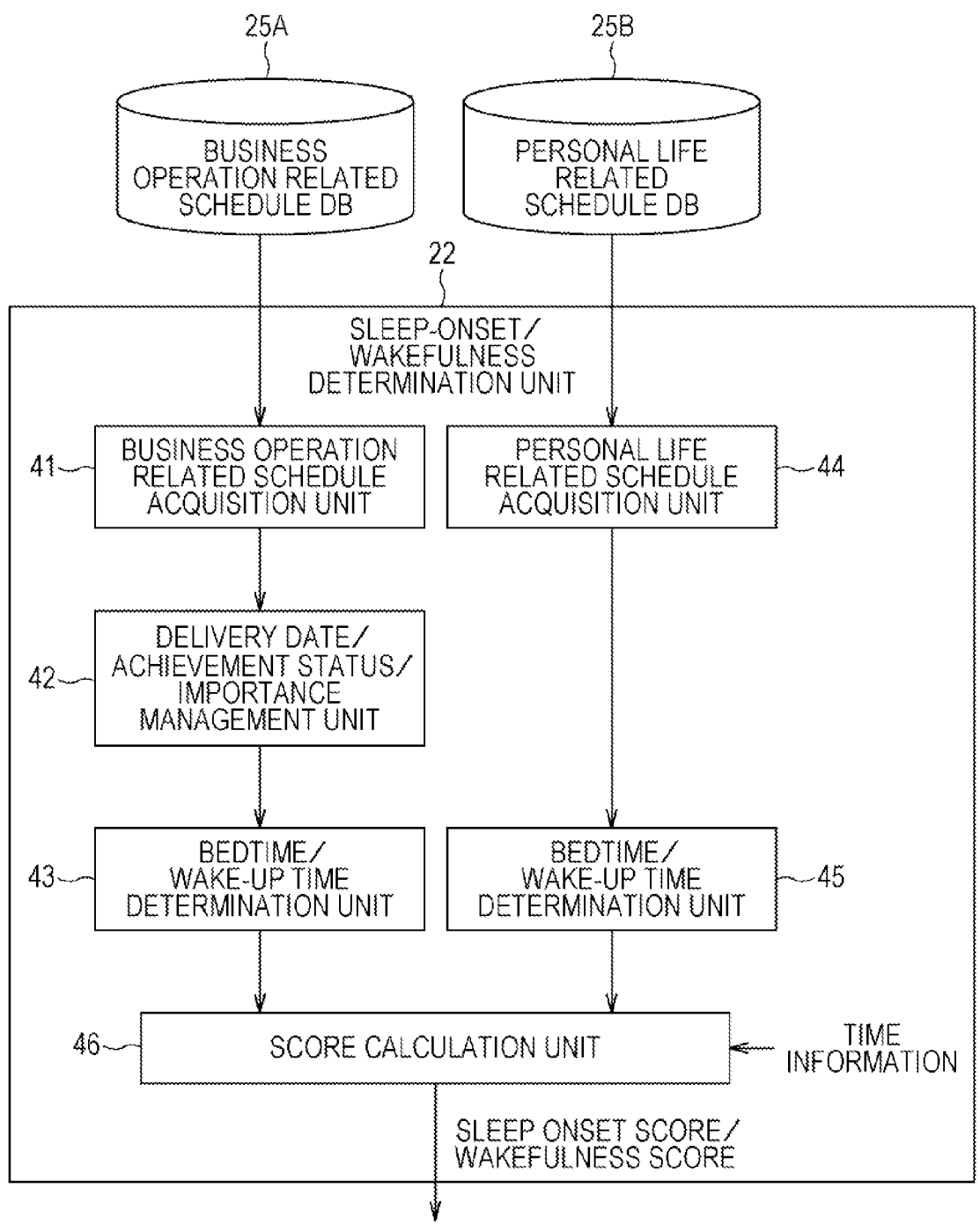
FIG. 9 is a block diagram illustrating an example structure of a sleep onset/wakefulness determination unit.

FIG. 9 is a block diagram illustrating an example structure of the sleep onset/wakefulness determination unit 22.

The sleep onset/wakefulness determination unit 22 has a business operation related schedule acquisition unit 41, a delivery deadline/achievement status/importance management unit 42, a bedtime/wake-up time determination unit 43, a personal life related schedule acquisition unit 44, a bedtime/wake-up time determination unit 45 and a score calculation unit 46.

The business operation related schedule acquisition unit 41 reads and acquires business operation related schedule information of the user from the business operation related schedule DB 25A which forms the schedule DB 25. A business operation related schedule includes, for example, a meeting start time, a business trip start time, a predetermined document creation deadline and a lunch time. The business operation related schedule acquisition unit 41 outputs the acquired schedule information to the delivery deadline/achievement status/importance management unit 42.

The delivery deadline/achievement status/importance management unit 42 manages information such as a product delivery deadline, an achievement status of work and importance of each item registered as a schedule. The information managed by the delivery deadline/achievement status/importance management unit 42 is set by, for example, the user.

The delivery deadline/achievement status/importance management unit 42 outputs the schedule information supplied from the business operation related schedule acquisition unit 41 to the bedtime/wake-up time determination unit 43 together with the information such as the product delivery deadline, the achievement status of work and the importance of the schedule. When, for example, receiving a supply of information including the meeting start time from the business operation related schedule acquisition unit 41, the delivery deadline/achievement status/importance management unit 42 outputs information of this meeting importance together with the information supplied from the business operation related schedule acquisition unit 41.

The bedtime/wake-up time determination unit 43 acquires the information supplied from the delivery deadline/achievement status/importance management unit 42, and determines whether the user needs to wake up or sleep, according to the schedule. The bedtime/wake-up time determination unit 43 determines a wake-up time when determining that the user needs to wake up, and determines a bedtime when determining that the user needs to sleep.

When, for example, specifying that there is a time until a next meeting start time, the bedtime/wake-up time determination unit 43 determines that the user needs to sleep. Further, the bedtime/wake-up time determination unit 43 determines as a wake-up time a time which is a predetermined time before the next meeting start time. The bedtime/wake-up time determination unit 43 outputs information of the wake-up time or the bedtime determined in this way to the score calculation unit 46.

The personal life related schedule acquisition unit 44 reads and acquires personal life related schedule information of the user from the personal life related schedule DB 25B of the schedule DB 25. The personal life related schedule includes, for example, a usual wake-up time, the bedtime and the nearest station of the user. The personal life related schedule acquisition unit 44 outputs the acquired schedule information to the bedtime/wake-up time determination unit 45.

The bedtime/wake-up time determination unit 45 acquires the schedule information supplied from the personal life related schedule acquisition unit 44, and determines whether the user needs to wake up or needs to sleep, according to the schedule. The bedtime/wake-up time determination unit 45 determines the wake-up when determining that the user needs to wake up, and determines the bedtime when determining that the user needs to sleep.

When, for example, acquiring schedule information including the usual wake-up time of the user and the current time comes close to the wake-up time, the bedtime/wake-up time determination unit 45 determines that the user needs to wake up. The bedtime/wake-up time determination unit 45 determines as a wake-up time a time which is a predetermined before the usual wake-up time. The bedtime/wake-up time determination unit 45 outputs information of the wake-up time or the bedtime determined in this way, to the score calculation unit 46.

When the bedtime/wake-up time determination unit 43 or the bedtime/wake-up time determination unit 45 determines the wake-up time, the score calculation unit 46 calculates a wakefulness score based on the wake-up time and the current time. Meanwhile, when the bedtime/wake-up time determination unit 43 or the bedtime/wake-up time determination unit 45 determines the bedtime, the score calculation unit 46 calculates a sleep onset score based on the wake-up time and the current time.

When, for example, the wake-up time determined by the bedtime/wake-up time determination unit 43 or the bedtime/wake-up time determination unit 45 is a time which is ten minutes after the current time, the score calculation unit 46 calculates a higher wakefulness score than a wakefulness score when the wake-up time is a time which is thirty minutes after the current time. Thus, the score calculation unit 46 calculates a wakefulness score by calculating a lower score when a time from the current time to the wake-up time is longer and calculating a higher score when the time from the current time to the wake-up time is shorter.

Similarly, when the bedtime determined by the bedtime/wake-up time determination unit 43 or the bedtime/wake-up time determination unit 45 is a time which is ten minutes after the current time, the score calculation unit 46 calculates a higher sleep onset score than a sleep onset score when the bedtime is a time which is thirty minutes after the current time. Thus, the score calculation unit 46 calculates a sleep onset score by calculating a lower score when the time from the current time to the bedtime is longer and, by contrast with this, calculating a higher score when the time from the current time to the sleep onset time is shorter.

The score calculation unit 46 outputs the calculated sleep onset score or wakefulness score to the music selection/playback unit 24.

Figure 10:
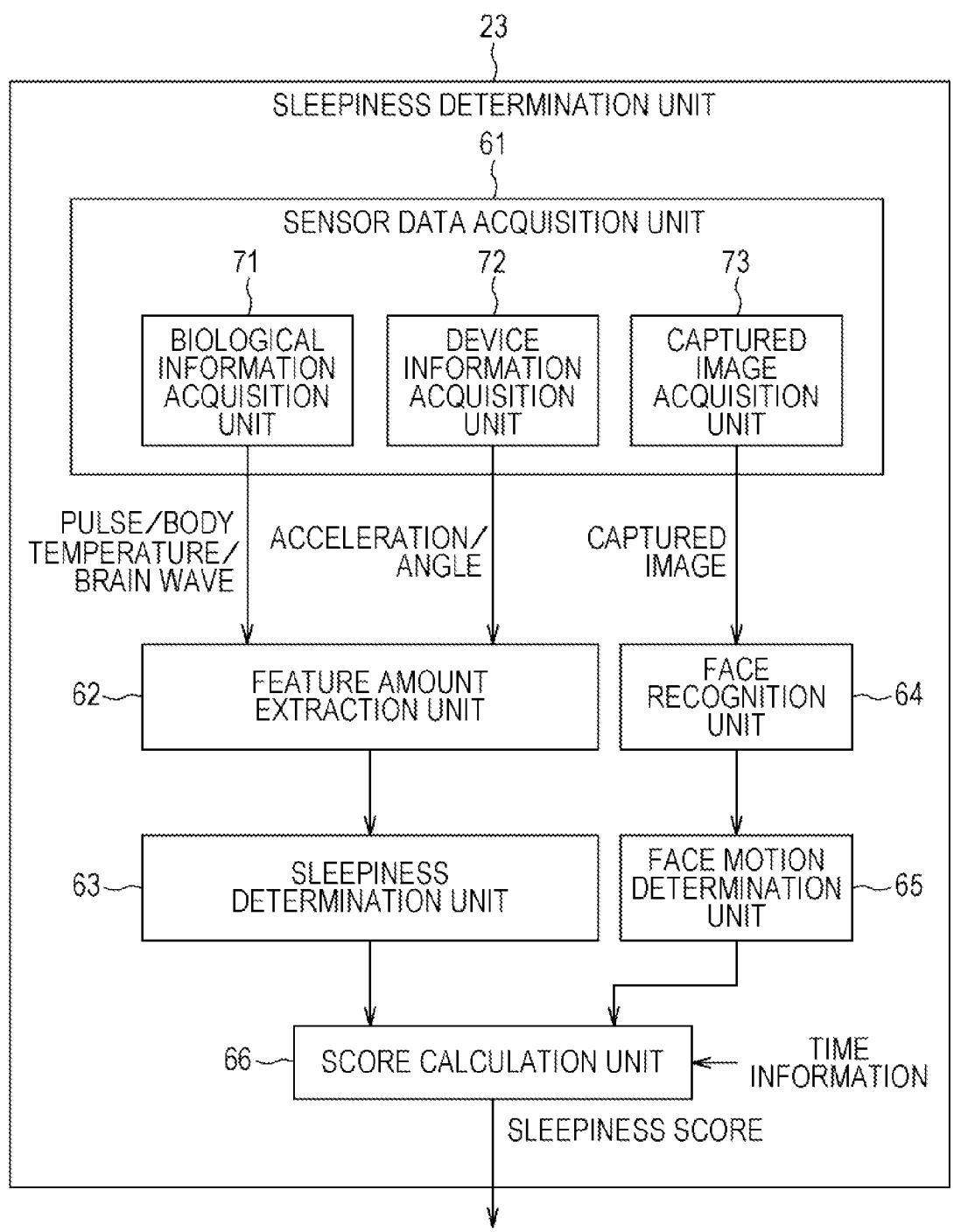
FIG. 10 is a block diagram illustrating an example structure of a sleepiness determination unit.

FIG. 10 is a block diagram illustrating an example structure of the sleepiness determination unit 23.

The sleepiness determination unit 23 is formed with a sensor data acquisition unit 61, a feature amount extraction unit 62, a sleepiness determination unit 63, a face recognition unit 64, a face motion determination unit 65 and a score calculation unit 66. The sensor data acquisition unit 61 is formed with a biological information acquisition unit 71, a device information acquisition unit 72 and a captured image acquisition unit 73.

The biological information acquisition unit 71 of the sensor data acquisition unit 61 acquires sensor data outputted from a sensor which detects biological information of the sensor which forms the sensor unit 12. The biological information acquisition unit 71 outputs biological information which is information of the pulse of the user detected by the pulse sensor, the body temperature of the user detected by the body temperature sensor and the brain wave of the user detected by the brain wave sensor, to the feature amount extraction unit 62.

The device information acquisition unit 72 acquires sensor data outputted from the sensor which detects device information of the sensor which forms the sensor unit 12. The device information acquisition unit 72 outputs device information which is information of the acceleration detected by the acceleration sensor and the angle detected by the gyro sensor, to the feature amount extraction unit 62.

The captured image acquisition unit 73 acquires an image of a face of the user captured by the camera 13, and outputs the image to the face recognition unit 64.

The feature amount extraction unit 62 analyzes the biological information supplied from the biological information acquisition unit 71, and extracts the feature amount of the biological information. Further, the feature amount extraction unit 62 analyzes the device information supplied from the device information acquisition unit 72, and extracts the feature amount of the device information. The feature amount extraction unit 62 outputs the extracted feature amount of the biological information and feature amount of the device information to the sleepiness determination unit 63.

The sleepiness determination unit 63 is a sleepiness determinator which determines sleepiness of the user by matching teacher data given in advance and the feature amount supplied from the sleepiness determination unit 63. The sleepiness determination unit 63 receives, for example, the feature amount extracted from the biological information obtained when a person is sleeping, and the feature amount extracted from the device information as teacher data.

The sleepiness determination unit 63 calculates a matching score by matching teacher data of the biological information and the feature amount extracted from the biological information by the feature amount extraction unit 62. Further, the sleepiness determination unit 63 calculates a matching score by matching the teacher data of the device information and the feature amount extracted from the device information by the feature amount extraction unit 62. For example, the sleepiness determination unit 63 outputs the calculated matching score to the score calculation unit 66 as information which indicates sleepiness of the user.

In addition, the sleepiness determination unit 63 determines sleepiness using at least part of sensor data of a plurality of items of sensor data included in the biological information and the device information. When, for example, the user is out and biological information cannot be acquired, sleepiness of the user is determined based only on device information.

The face recognition unit 64 analyzes the image acquired by the captured image acquisition unit 73, and recognizes the face of the user shown in the image. Further, the face recognition unit 64 extracts a feature of the recognized face, and outputs the feature to the face motion determination unit 65. For example, the feature of the eyes of the user is extracted by the face recognition unit 64.

The face motion determination unit 65 determines a motion of the face of the user which is a reference to determine whether or not the user is sleeping such as whether or not the eyes of the user are open or the user is blinking, based on the feature amount supplied from the face recognition unit 64. The face motion determination unit 65 outputs information which indicates a determination result of the motion of the face of the user to the score calculation unit 66.

As a determination result of the motion of the face of the user, for example, a score which indicates a likelihood that the eyes of the user are open or not open or a score which indicates a likelihood that the user is blinking or is not blinking is outputted to the score calculation unit 66. When, for example, the number of times of blinking of the user per predetermined unit time is less than a threshold number of times, it is determined that the user is highly likely to be sleepy.

The score calculation unit 66 calculates a sleepiness score based on the information which indicates sleepiness of the user supplied from the sleepiness determination unit 63 and the determination result of the motion of the face of the user supplied from the face motion determination unit 65. The current time is also taken into account to calculate the sleepiness score. The score calculation unit 66 outputs information of the calculated sleepiness score to the music selection/playback unit 24.

Techniques of detecting sleepiness of people based on, for example, biological information are disclosed in, for example, Japanese Patent Application Laid-Open No. 2011-48531 and Japanese Patent Application Laid-Open No. 2011-22738.

Figure 11:
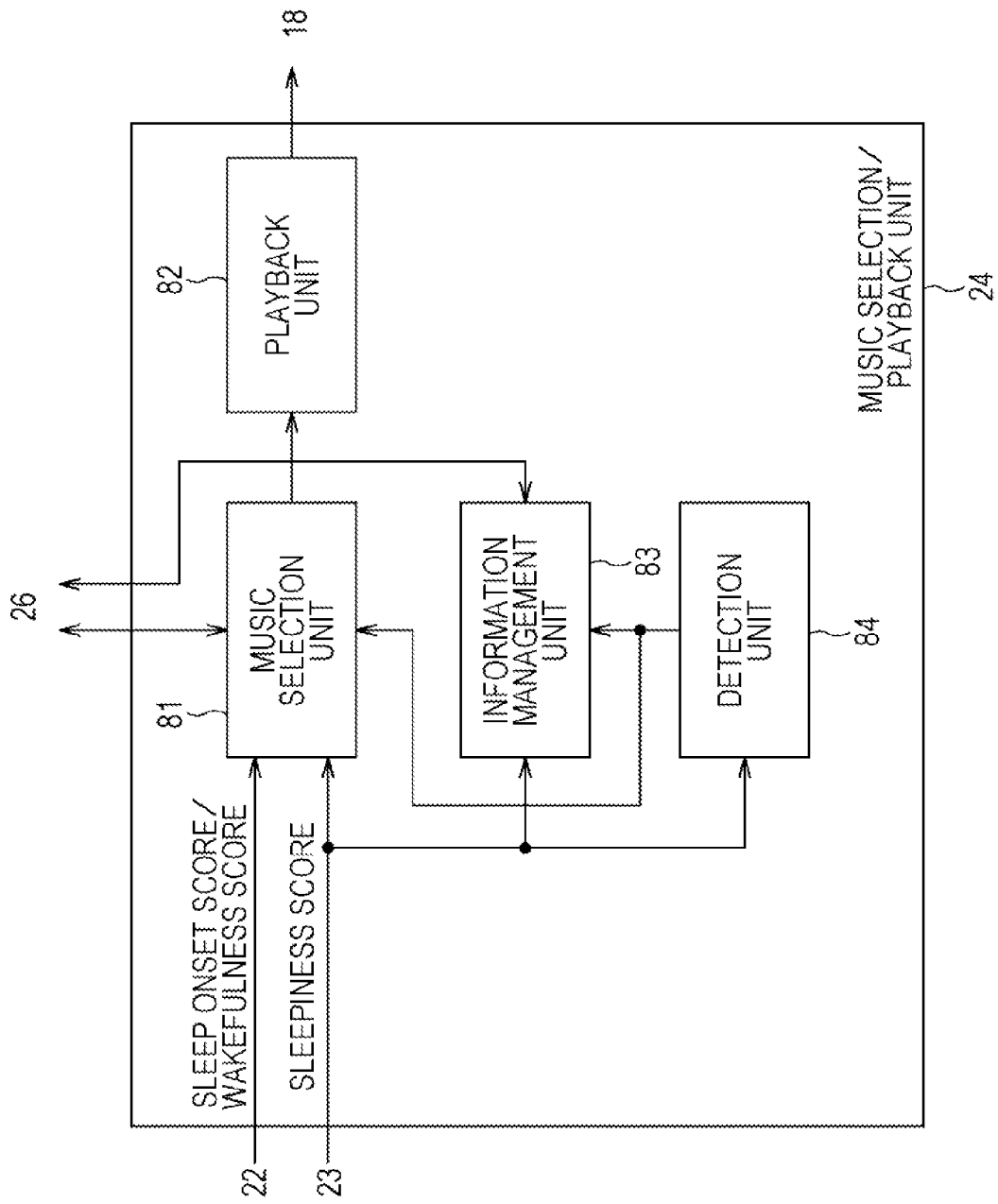
FIG. 11 is a block diagram illustrating an example structure of a music selection/playback unit.

FIG. 11 is a block diagram illustrating an example structure of the music selection/playback unit 24.

The music selection/playback unit 24 has a music selection unit 81, a playback unit 82, an information management unit 83 and a detection unit 84. The sleep onset score or the wakefulness score supplied from the sleep onset/wakefulness determination unit 22 is inputted to the music selection unit 81, and a sleepiness score supplied from the sleepiness determination unit 23 is inputted to the music selection unit 81, the information management unit 83 and the detection unit 84.

The music selection unit 81 selects music to playback from music stored in the music DB 26 based on the sleep onset score or the wakefulness score supplied from the sleep onset/wakefulness determination unit 22 and the sleepiness score supplied from the sleepiness determination unit 23. The music selection unit 81 reads data of the selected music from the music DB 26, and outputs the data to the playback unit 82.

The playback unit 82 plays back the music selected by the music selection unit 81, and outputs a sound obtained by playing back the music, to the playback sound output unit 18.

The information management unit 83 updates meta data of the music played back based on the sleepiness score before the music is played back by the playback unit 82 and the sleepiness score calculated from sensor data detected after the music is played back. Meta data is updated when, for example, it is detected that the user fell asleep by playing back music or when the user woke up by playing back music.

The detection unit 84 detects whether or not the user is awake or is sleeping based on the inputted sleepiness score. When detecting that the user fell asleep by playing back music in case that it is determined that the user needs to sleep, the detection unit 84 outputs this detection result to the music selection unit 81 and the information management unit 83. Further, when detecting that the user woke up by playing back music in case that it is determined that the user needs to wake up, the detection unit 84 outputs this detection result to the music selection unit 81 and the information management unit 83.

Selection of music performed by the music selection unit 81, update of meta data performed by the information management unit 83 and detection of a user state performed by the detection unit 84 will be described below.

3. Operation of Information Processing Device

Next, an operation of the information processing device 1 employing the above configuration will be described.

First Embodiment (Example of Comfortable Wake-Up)

An operation in case of use case 1 where music is played back for a wake-up time in the morning to comfortably wake up the user will be described.

Figure 12:
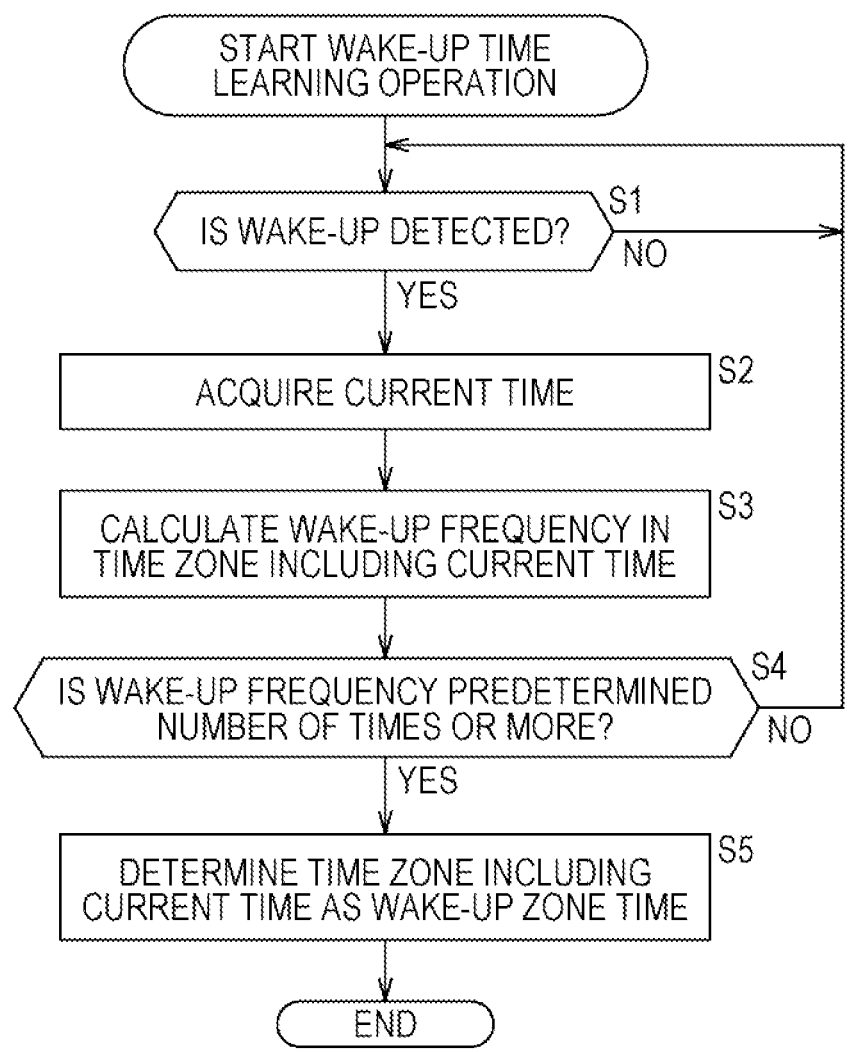
FIG. 12 is a flowchart for explaining an operation of learning a wake-up time of a user.

First, the operation of an information processing device 1 which learns a usual wake-up time of the user will be described with reference to a flowchart in FIG. 12. An operation in FIG. 12 is performed after, for example, the wake-up time is set by an alarm function of the information processing device 1. When the wake-up time comes, a control unit 21 outputs an alarm sound from a playback sound output unit 18.

In step S1, the control unit 21 determines whether or not wake-up of the user is detected, and stands by until it is determined that wake-up is detected. Whether or not the user woke up is detected based on whether or not the user performs an operation of stopping the alarm sound. Whether or not the user woke up may be determined based on a sleepiness score or sensor data as described below.

When it is determined in step S1 that wake-up of the user is detected since the operation of stopping the alarm sound was performed, the control unit 21 acquires the current time in step S2.

In step S3, the control unit 21 calculates a wake-up frequency of a time zone including the current time. For example, the control unit 21 stores a history of every day wake-up times of the user in a schedule DB 25, and manages the history. The control unit 21 calculates the wake-up frequency of the time zone including the current time of a predetermined time zone such as every fifteen minute based on the history stored in the schedule DB 25.

In step S4, the control unit 21 determines whether or not the wake-up frequency of the time zone including the current time is a predetermined number of times or more which is a threshold. When it is determined in step S4 that the wake-up frequency of the time zone including the current time is less than a predetermined number of times, the operation returns to step S1 and the above operation is repeated.

Meanwhile, when it is determined in step S4 that the wake-up frequency of the time zone including the current time is a predetermined number of times or more, the control unit 21 determines the time zone including the current time as a wake-up time zone in step S5. The control unit 21 sets a predetermined time of the wake-up time zone such as a start time of the determined wake-up time zone as a wake-up time, and stores information of the wake-up time in the personal life related schedule DB 25B of the schedule DB 25. Subsequently, the operation is finished.

Figure 13:
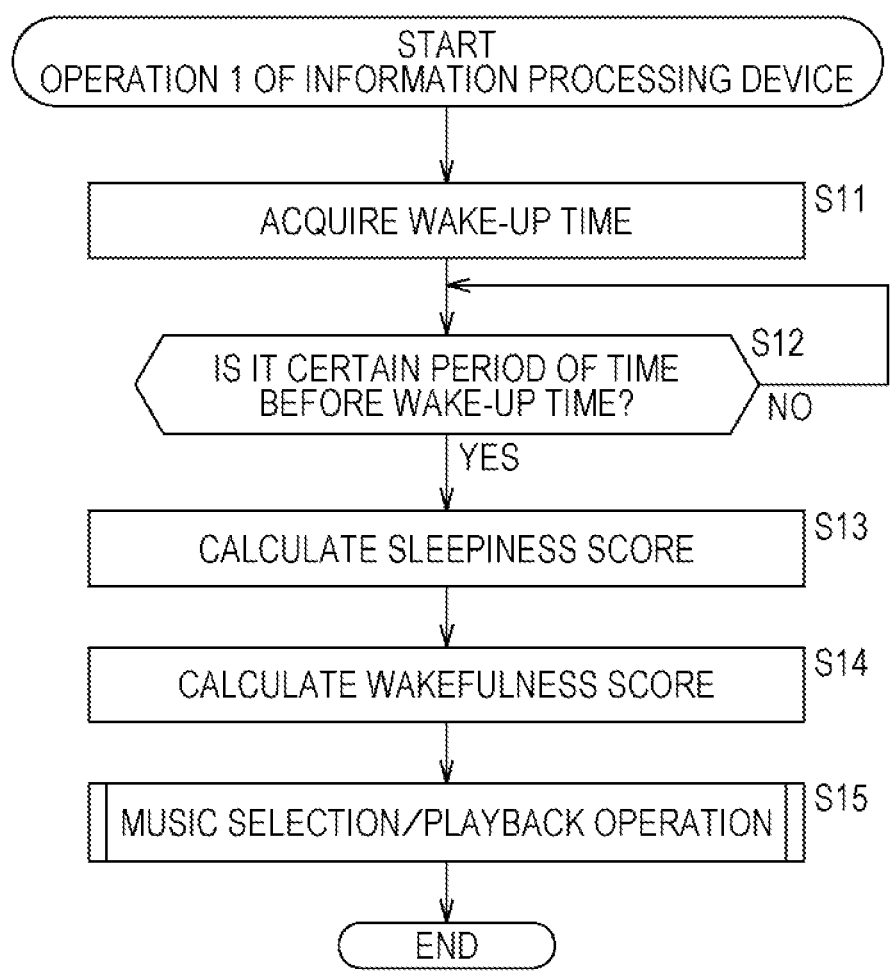
FIG. 13 is a flowchart for explaining an operation in case of use case 1.

Next, the operation of the information processing device 1 of playing back music at a wake-up time of the user will be described with reference to a flowchart in FIG. 13. The operation in FIG. 13 is performed when, for example, the user is sleeping.

In step S11, a personal life related schedule acquisition unit 44 (FIG. 9) of a sleep onset/wakefulness determination unit 22 acquires information of the usual wake-up time obtained by learning, from the personal life related schedule DB 25B. A bedtime/wake-up time determination unit 45 determines as a wake-up time a usual wake-up time which is acquired from the personal life related schedule DB 25B.

In step S12, a score calculation unit 46 determines that the user needs to wake up, and determines whether or not the current time is a time which is a fixed time before the wake-up time. The score calculation unit 46 stands by until it is determined in step S12 that the current time is a time which is a fixed time before the wake-up time.

When it is determined in step S12 that the current time is the time which is the fixed time before the wake-up time, a sleepiness determination unit 23 calculates a sleepiness score based on the sensor data detected by a sensor unit 12 in step S13.

In step S14, the score calculation unit 46 of the sleep onset/wakefulness determination unit 22 calculates a wakefulness score.

In step S15, a music selection/playback unit 24 performs a music selection/playback operation. According to the music selection/playback operation, music which can cause a change of sleepiness in the user such that a sleepiness score is close to the wakefulness score, and is played back. The music selection/playback operation will be described below. After the music selection/playback operation is performed and the user wakes up, the operation is finished.

According to the above operation, the information processing device 1 can comfortably wake up the user by playing back music of a slow pace when sleepiness of the user is a little.

Second Embodiment (Example of Prevention of Oversleep on Train)

An operation in case of use case 2 that music is played back as a user comes close to the nearest station and is prevented from oversleeping on a train will be described.

Figure 14:
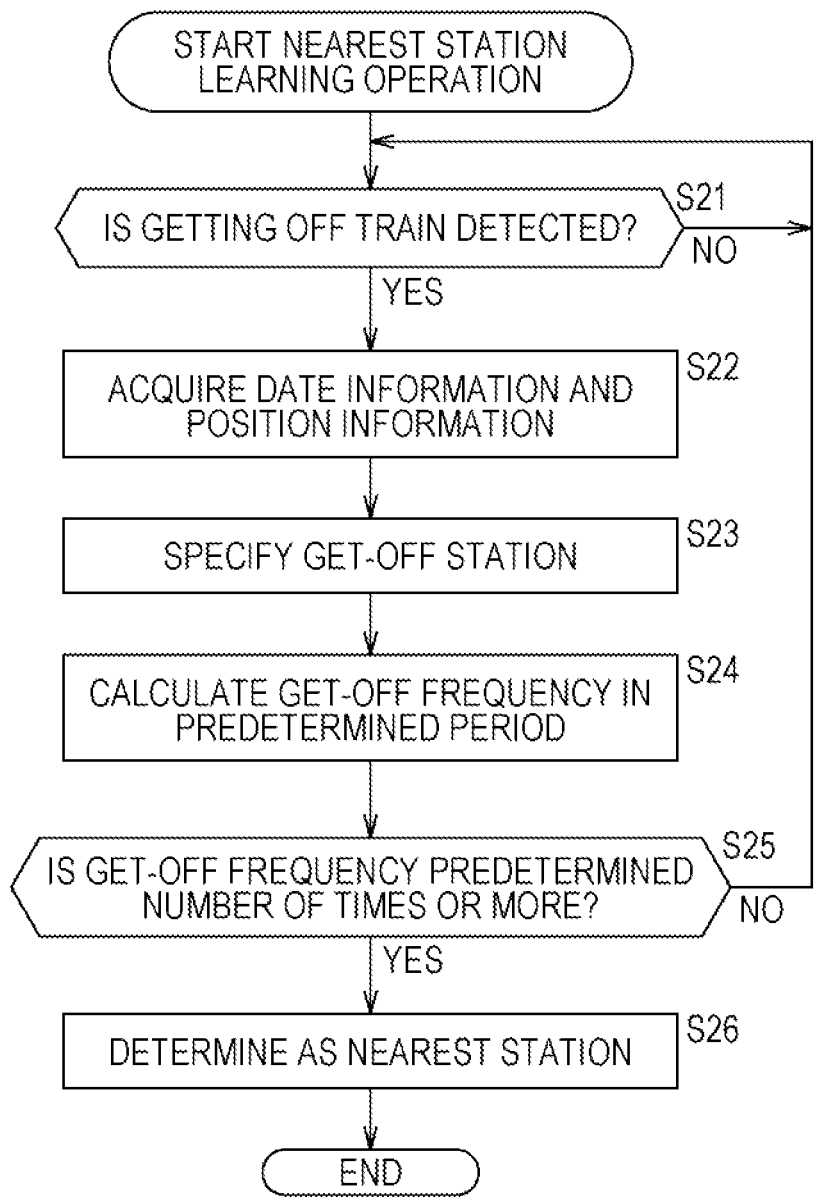
FIG. 14 is a flowchart for explaining an operation of learning a nearest station of a user.

First, the operation of an information processing device 1 of learning the nearest station of the user will be described with reference to a flowchart in FIG. 14. The operation in FIG. 14 is started when, for example, it is detected that the user is on the train.

It is detected that the user is on the train when, for example, a current position detected by a GPS is a position on a train track, and a moving speed of the position has a speed equal to the speed of the train. Further, that the user is on a train can be detected when a feature of vibration detected by a sensor unit 12 matches with a feature of vibration detected in the train. Information which indicates the speed of the train and a feature of vibration detected in the train is stored in, for example, a storage unit 16 in advance. According to the user's operation, that the user is on the train may be detected.

In step S21, a control unit 21 determines whether or not that the user got off the train is detected, and stands by until it is determined that the user got off the train. It is detected that the user got off the train when, for example, a current position detected by a GPS is a position on a train station, and a moving speed is a walking speed. According to the user's operation, that the user got off the train may be detected.

In step S22, the control unit 21 acquires date information and position information. The position information is acquired by the GPS.

In step S23, the control unit 21 specifies a get-off station based on the acquired position information. For example, the control unit 21 specifies on a map the position indicated by the position information, and, when the specified position is the position of the station, specifies this station as the get-off station. The map provided in the control unit 21 in advance includes information of the position of each station.

In step S24, the control unit 21 calculates a get-off frequency in a predetermined period at the specified get-off station. For example, the control unit 21 specifies the get-off station every day, and stores a history of get-off stations in a schedule DB 25 and manages the history. The control unit 21 calculates the get-off frequency in a predetermined period such as one week based on the history stored in the schedule DB 25.

In step S25, the control unit 21 determines whether or not the get-off frequency calculated in step S24 is a predetermined number of times or more. When it is determined in step S25 that the get-off frequency is less than a predetermined number of times, the operation returns to step S21 and the above operation is repeated.

Meanwhile, when it is determined in step S25 that the get-off frequency is a predetermined number of times or more, the control unit 21 determines the specified get-off station as the nearest station in step S26. The control unit 21 stores information of the nearest station in the personal life related schedule DB 25B of the schedule DB 25, and the operation is finished.

Next, the operation of the information processing device 1 of playing back music when the user gets off a train will be described with reference to a flowchart in FIG. 15.

In step S31, the control unit 21 determines whether or not the user got on a train, and stands by until it is determined that the user got on the train. Whether or not the user is on the train is determined using, for example, the current position detected by the GPS as described above and the map.

When it is determined in step S31 that the user got on a train, a personal life related schedule acquisition unit 44 acquires information of a time table of the train which the user got on in step S32. The train which the user got on is detected based on, for example, a position of a departure station and a moving direction of the user detected by the GPS. The information of the time table of the train which the user got on is downloaded from a predetermined server in advance, and is stored in a personal life related schedule DB 25B.

In step S33, a bedtime/wake-up time determination unit 45 refers to the time table acquired by a personal life related schedule acquisition unit 44, and specifies the time at which the train which the user is on arrives at the nearest station. A score calculation unit 46 determines the specified arrival time as a get-off time, that is, a wake-up time of the user sleeping on the train.

In step S34, the score calculation unit 46 determines whether or not the current time is a time which is a fixed time before the get-off time, and stands by until it is determined that the current time is the time which is the fixed time before the get-off time.

When it is determined in step S34 that the current time is the time which is the fixed time before the get-off time, a sleepiness determination unit 23 calculates a sleepiness score based on the sensor data detected by the sensor unit 12 in step S35.

In step S36, the score calculation unit 46 calculates a wakefulness score.

In step S37, a music selection/playback unit 24 performs a music selection/playback operation. According to this music selection/playback operation, music which causes a significant change of sleepiness compared to use case 1 is selected, and is played back. After the music selection/playback operation is performed and the user wakes up, the operation is finished.

According to the above operation, the information processing device 1 can wake up the user before a train arrives at the nearest station by playing back music which causes a significant change of sleepiness.

Third Embodiment (Example of Early Bedding)

Next, the operation of an information processing device 1 in use case 3 where music is played back at a recommended bedtime to wake up a user early will be described with reference to a flowchart in FIG. 16.

In step S41, a business operation related schedule acquisition unit 41 of a sleep onset/wakefulness determination unit 22 acquires a next morning wake-up time of the user. When, for example, schedule information including the next wake-up time is stored in a business operation related schedule DB 25A of a schedule DB 25, the business operation related schedule acquisition unit 41 acquires the next morning wake-up time from this schedule information. When schedule information of a person accompanying the user of the information processing device 1 during a business trip is registered in the business operation related schedule DB 25A, the wake-up time of the user of the information processing device 1 may be acquired based on this schedule information.

In step S42, a bedtime/wake-up time determination unit 43 calculates a recommended bedtime according the wake-up time acquired in step S41. For example, the bedtime/wake-up time determination unit 43 calculates as the recommended bedtime a time which is a predetermined time before the wake-up time acquired in step S41.

When terminals of accompanying a person detect that the accompanying person is sleeping and information of this detection result is received by the information processing device 1 through a server, the recommended bedtime may be calculated. For example, a time which is a predetermined time after a time when the accompanying person falls asleep is calculated as the recommended bedtime. Importance of a schedule in the next morning managed by a delivery deadline/achievement status/importance management unit 42 is also adequately taken into account to determine the recommended bedtime.

In step S43, the bedtime/wake-up time determination unit 43 determines whether or not the current time is a time which is a fixed time before the recommended bedtime. The bedtime/wake-up time determination unit 43 stands by until it is determined in step S43 that the current time is a time which is a fixed time before the recommended bedtime.

When it is determined in step S43 that the current time is the time which is the fixed time before the recommended bedtime, the sleepiness determination unit 23 calculates a sleepiness score based on the sensor data detected by a sensor unit 12 in step S44.

In step S45, the score calculation unit 46 calculates a sleep onset score.

In step S46, a music selection/playback unit 24 performs a music selection/playback operation. According to this music selection/playback operation, music which can cause a change of sleepiness in the user such that a sleepiness score becomes close to the sleep onset score is selected, and is played back. After the music selection/playback operation is performed and the user falls asleep, the operation is finished.

According to the above operation, the information processing device 1 can get the user to sleep at an early time by playing back music which increases sleepiness.

Fourth Embodiment (Example of Nap)

Next, the operation of an information processing device 1 in use case 4 where music is played back to get a user to take a nap during a time until a next meeting will be described with reference to a flowchart in FIG. 17.

In step S51, a business operation related schedule acquisition unit 41 of a sleep onset/wakefulness determination unit 22 acquires schedule information stored in a business operation related schedule DB 25A of a schedule DB 25. Meanwhile, for example, information including a start time of a next meeting is acquired. The information acquired by the business operation related schedule acquisition unit 41 is outputted to a score calculation unit 46 through a delivery deadline/achievement status/importance management unit 42 and a bedtime/wake-up time determination unit 43 together with information such as the importance of the meeting.

In step S52, the score calculation unit 46 calculates a sleep onset score when there is a spare time equal to or more than a predetermined time until the start time of the next meeting.

In step S53, a sleepiness determination unit 23 calculates a sleepiness score based on sensor data detected by a sensor unit 12.

In step S54, a music selection/playback unit 24 performs a music selection/playback operation. The music selection/playback operation in this case is an operation of getting the user to sleep, and the user who listens to music played back adequately takes a nap.

After the user starts taking a nap, in step S55, a bedtime/wake-up time determination unit 43 determines that the user needs to wake up, and sets a wake-up time. When, for example, a sleepiness score is higher, the wake-up time is a later time.

In step S56, the bedtime/wake-up time determination unit 43 determines whether or not the current time is a time which is a fixed time before the wake-up time, and stands by until it is determined that the current time is the time which is the fixed time before the wake-up time.

When it is determined in step S56 that the current time is the time which is the fixed time before the wake-up time, the sleepiness determination unit 23 calculates a sleepiness score based on the sensor data detected by the sensor unit 12 in step S57.

In step S58, the score calculation unit 46 calculates a wakefulness score.

In step S59, the music selection/playback unit 24 performs a music selection/playback operation. The music selection/playback operation in this case is an operation of waking up the user who is taking a nap, and the user who listens to music wakes up from the nap. After the music selection/playback operation is performed and the user wakes up, the operation is finished.

According to the above operation, the information processing device 1 can get the user to take a nap when there is a time until the next schedule, or wake up the user before the next schedule.

4. Music Selection/Playback Operation

Hereinafter, the music selection/playback operation performed in step S15 in FIG. 13, step S37 in FIG. 15, step S46 in FIG. 16 and steps S54 and S59 in FIG. 17 will be described with reference to a flowchart in FIG. 18.

In step S71, a music selection unit 81 of the music selection/playback unit 24 selects a music DB. The music DB includes a music DB 26 which is a personal DB in the information processing device 1 and, in addition, a large scale user DB which a plurality of users can access on a server. The information processing device 1 can acquire music data from the large user music DB, and plays back the music. For example, one of the music DB 26 which is the personal DB and the large scale user music DB is specified by the user and selected.

FIG. 19 is a view illustrating an example of meta data of music stored in the music DB. FIG. 19A illustrates the music DB 26 (personal music DB), and FIG. 19B illustrates the large scale user music DB.

As illustrated by FIG. 19A and FIG. 19B, in the music DB, music names, sleepiness score increase/decrease values, and sleep onset/wakefulness intensity (sleep onset intensity and wakefulness intensity) meta data are associated with each music and managed. The sleepiness score increase/decrease value is a value which represents a change of a sleepiness score which is caused in the user who listens to music. The sleep onset intensity indicates the degree of sleep onset, and the wakefulness intensity indicates the degree of wakefulness.

For example, that the sleepiness score increase/decrease value of music "A" in FIG. 19A is −10 means that, when the user of the information processing device 1 listens to the music "A", it is possible to decrease the sleepiness score of the user by 10, that is, it is possible to wake up the user by the value 10. In this case, the wakefulness intensity of the music "A" is 1.

Further, that the sleepiness score increase/decrease value of the music "B" in FIG. 19A is +50 means that, when the user of the information processing device 1 listens to the music "B", it is possible to increase the sleepiness score of the user by 50, that is, it is possible to get the user to sleep by a value 50. In this case, the sleep onset intensity of the music "B" is 3.

The sleepiness score increase/decrease value of the music DB 26 is registered in advance by detecting a change between sleepiness scores before and after, for example, the user listens to the music "A" and "B".

Further, the sleepiness score increase/decrease value of the large scale user music DB in FIG. 19B indicates an average value of changes between sleepiness scores before and after a plurality of users listens to the music "A" and the music "B". The music "A" and the music "B" are played back at terminals of respective users, the detected sleepiness score increase/decrease values are transmitted and an average value thereof is calculated and managed in a server.

FIG. 20 is a view illustrating an example of a correspondence between a sleepiness score increase/decrease value and a sleep onset/wakefulness intensity. Data of a transform table which represents the correspondence in FIG. 20 is managed by, for example, the music selection unit 81.

In an example in FIG. 20, the wakefulness intensity is 1 when the sleepiness score increase/decrease value is 0 to −25 and the wakefulness intensity is 2 when the sleepiness score increase/decrease value is −25 to −50. Further, the wakefulness intensity is 3 when the sleepiness score increase/decrease value is −50 to −75, the wakefulness intensity is 4 when the sleepiness score increase/decrease value is −75 to −100 and the wakefulness intensity is 5 when the sleepiness score increase/decrease value is −100 or more.

Meanwhile, the sleep onset intensity is 1 when the sleepiness score increase/decrease value is 0 to 25, and the sleep onset intensity is 2 when the sleepiness score increase/decrease value is 25 to 50. Further, the sleep onset intensity is 3 when the sleepiness score increase/decrease value is 50 to 75, the sleep onset intensity is 4 when the sleepiness score increase/decrease value is 75 to 100, and the sleep onset intensity is 5 when the sleepiness score increase/decrease value is 100.

Figure 18:
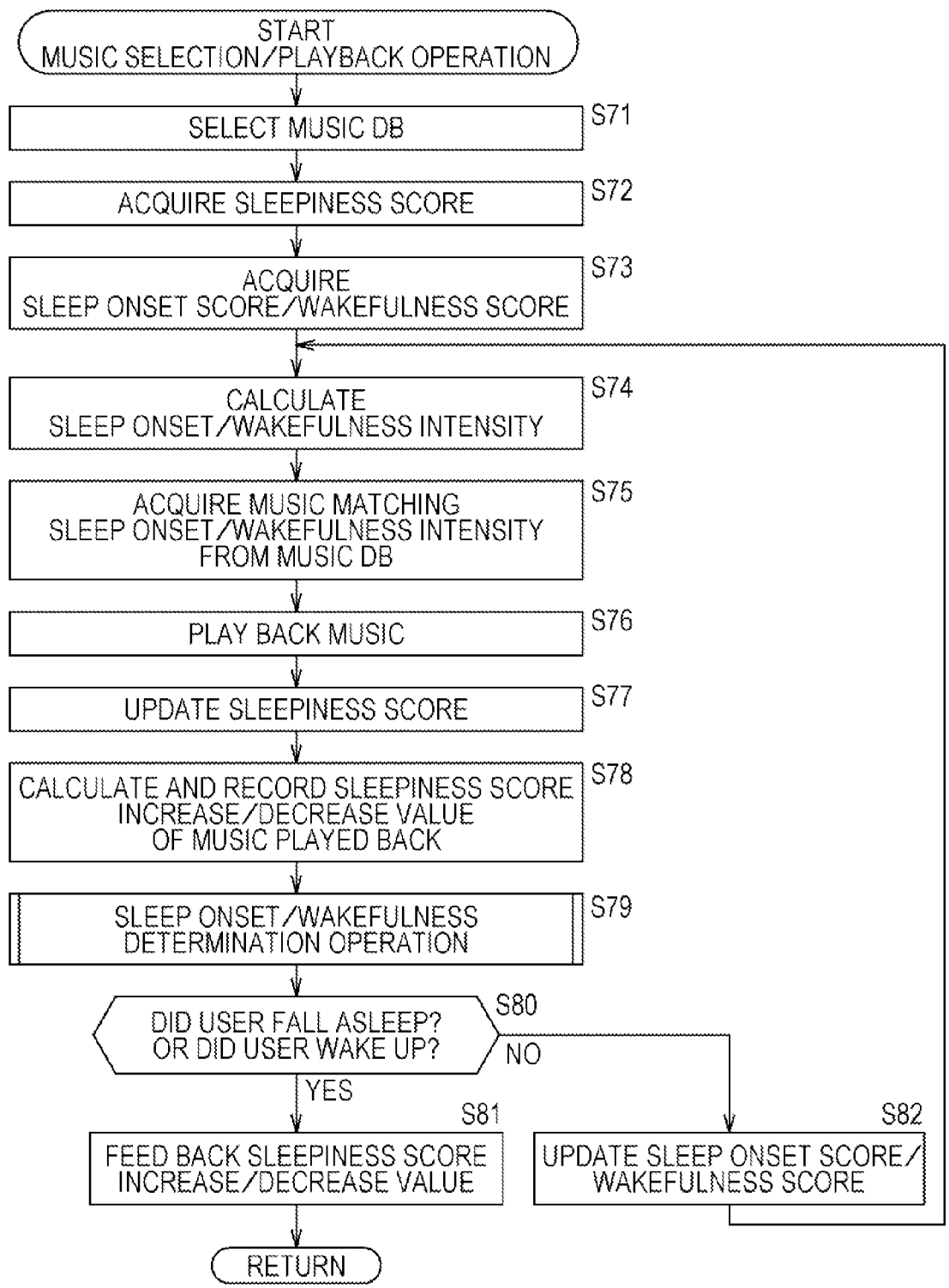
FIG. 18 is a flowchart for explaining a music selection/playback operation.

Back to description of FIG. 18, after the music DB is selected in step S71, the music selection unit 81 acquires a sleepiness score calculated by the sleepiness determination unit 23 in step S72. The sleepiness score calculated by the sleepiness determination unit 23 is also supplied to the information management unit 83.

In step S73, the music selection unit 81 acquires a sleep onset score or a wakefulness score calculated by the sleep onset/wakefulness determination unit 22.

In step S74, when the sleep onset score is calculated by the sleep onset/wakefulness determination unit 22, the music selection unit 81 calculates the sleep onset intensity based on the sleepiness score and the sleep onset score, and, when the wakefulness score is calculated by the sleep onset/wakefulness determination unit 22, calculates the wakefulness intensity based on the sleepiness score and the wakefulness score. As described above, the sleep onset score or the wakefulness score is regarded as an ideal sleepiness score of the user. The music selection unit 81 calculates the difference between the sleep onset score and the sleepiness score, and finds a sleep onset intensity of a sleepiness score increase/decrease value corresponding to the calculated difference, from the conversion table in FIG. 19. Further, the music selection unit 81 calculates the difference between the wakefulness score and the sleepiness score, and finds a wakefulness intensity of a sleepiness score increase/decrease value corresponding to the calculated difference, from the conversion table in FIG. 19.

When, for example, the sleepiness score of the user is 50 and the sleepiness score is −20, the music selection unit 81 calculates −70 which is a difference between the sleep onset score and the sleepiness score, and finds the wakefulness intensity 3 which is the wakefulness intensity corresponding toe sleepiness score increase/decrease value of −70.

In step S75, the music selection unit 81 selects music which includes as meta data the sleep onset intensity or the wakefulness intensity calculated in step S74 from music registered in the music DB selected in step S71, and acquires data. The music selected in this way is music which changes the sleepiness score of the user to an ideal sleepiness score. The music data selected by the music selection unit 81 and acquired from the music DB is supplied to the playback unit 82.

In step S76, the playback unit 82 plays back music selected by the music selection unit 81.

In step S77, the sleepiness determination unit 23 calculates again a sleepiness score of the user based on sensor data detected by the sensor unit 12 after the music is played back, and updates the sleepiness score. Generally, the updated sleepiness score becomes close to a sleep onset score or a wakefulness score from the sleepiness score before the music is played back. The updated sleepiness score is also supplied to the information management unit 83 and the detection unit 84.

In step S78, the information management unit 83 calculates as a sleepiness score increase/decrease value a difference between the sleepiness score after the music is played back and the sleepiness score before the music is played back, and records the sleepiness score increase/decrease value in, for example, a memory which is not illustrated.

In step S79, the detection unit 84 performs a sleep onset/wakefulness determination operation. The sleep onset/wakefulness determination operation is an operation of detecting that the user fell asleep when it is determined that the user needs to sleep, and is an operation of detecting that the user woke up when it is determined that the user needs to wake up. The sleep onset/wakefulness determination operation will be described below.

In step S80, the information management unit 83 determines whether the user fell asleep or woke up, based on a result of the sleep onset/wakefulness determination operation.

When it is determined that the user needs to sleep and it is determined in step S80 that the user fell asleep or when it is determined that the user needs to wake up and it is determined in step S80 that the user woke up, the information management unit 83 feeds back a sleepiness score increase/decrease value recorded in the memory in step S81.

The sleepiness score increase/decrease value is fed back by updating the sleepiness score increase/decrease value set to music played back as meta data based on a new sleepiness score increase/decrease value recorded in the memory.

When, for example, the music played back is music selected from the music DB 26, a sleepiness score increase/decrease value of this music is rewritten to a new sleepiness score increase/decrease value. Further, when music played back is music selected from the large scale user music DB, a sleepiness score increase/decrease value of this music is transmitted to the server. In the server, an average value of sleepiness score increase/decrease values of a plurality of users is calculated again based on the new sleepiness score increase/decrease value transmitted from the information processing device 1, and metal data of the music is rewritten.

Figure 15:
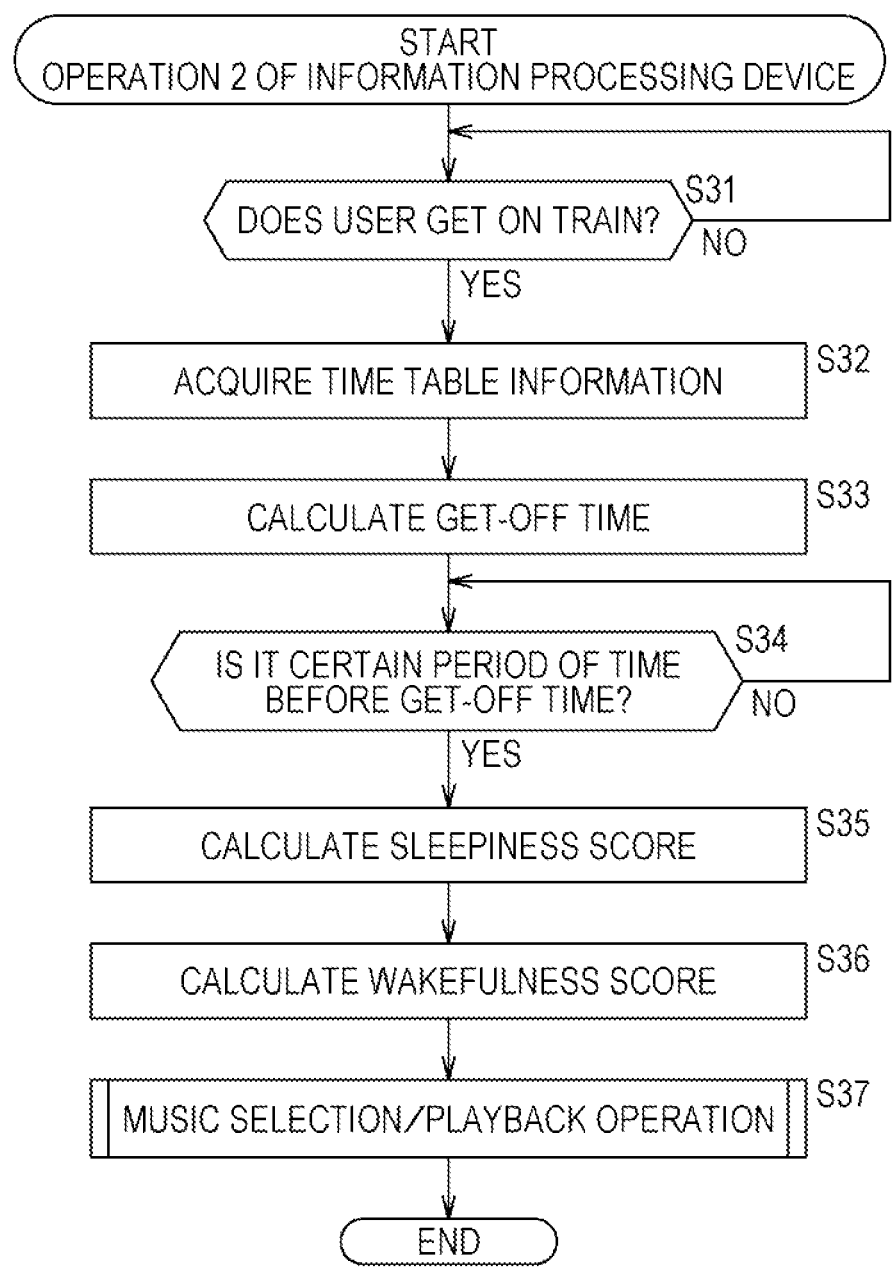
FIG. 15 is a flowchart for explaining an operation in case of use case 2.
Figure 16:
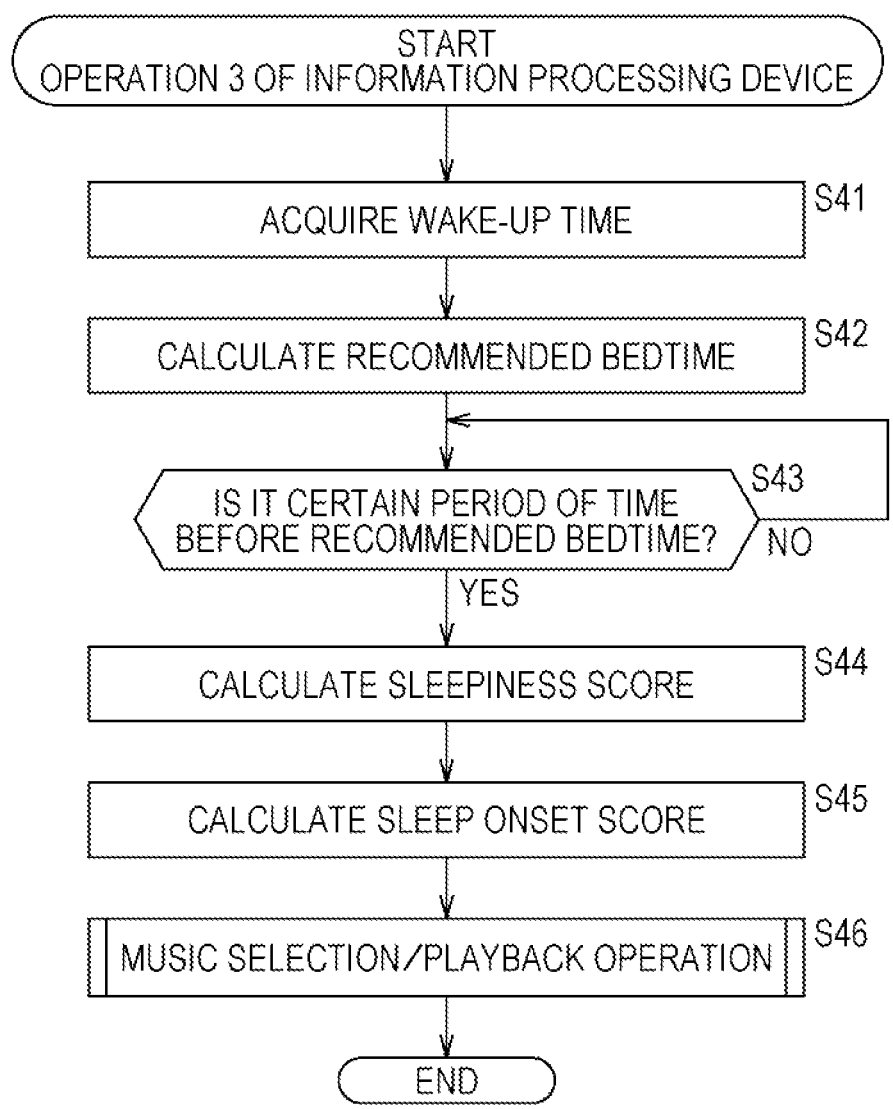
FIG. 16 is a flowchart for explaining an operation in case of use case 3.
Figure 17:
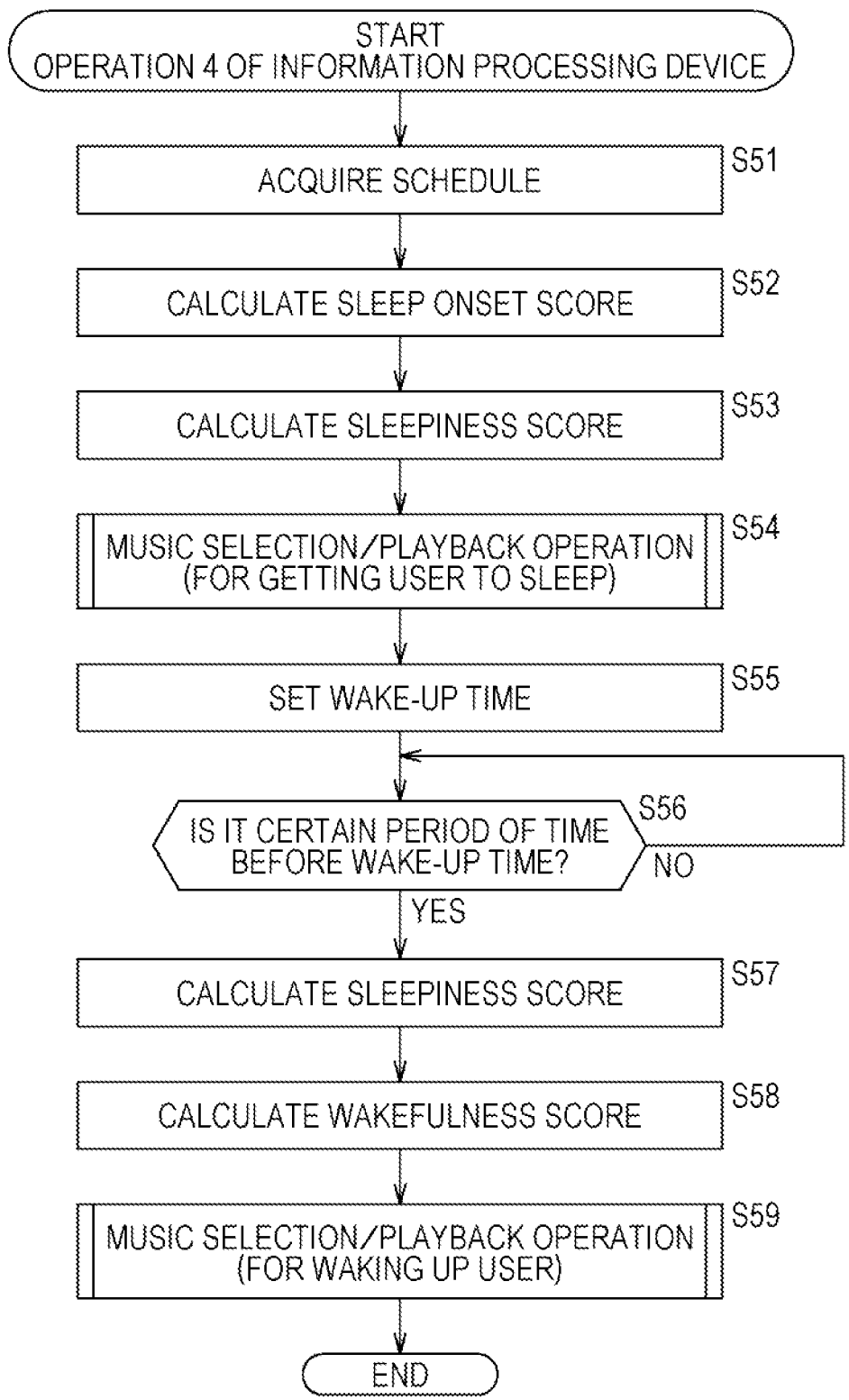
FIG. 17 is a flowchart for explaining an operation in case of use case 4.

After the sleepiness score increase/decrease value is fed back, the operation returns to each operation in step S15 in FIG. 13, step S37 in FIG. 15, step S46 in FIG. 16 and steps S54 and S59 in FIG. 17, and subsequent operations are performed.

Meanwhile, when it is determined in step S80 that the user is not sleeping or is not awake, the score calculation unit 46 of the sleep onset/wakefulness determination unit 22 calculates again and updates the sleep onset score or the wakefulness score in step S82. After the sleep onset score or the wakefulness score is updated, operations subsequent to step S74 are performed. When, for example, the user does not wake up even if music for waking up the user is played back, the wakefulness score is updated to a higher wakefulness score as the current time comes close to the wake-up time, and the operations subsequent to step S74 are performed.

Meanwhile, the sleep onset/wakefulness determination operation performed in step S79 in FIG. 18 will be described.

Figure 21:
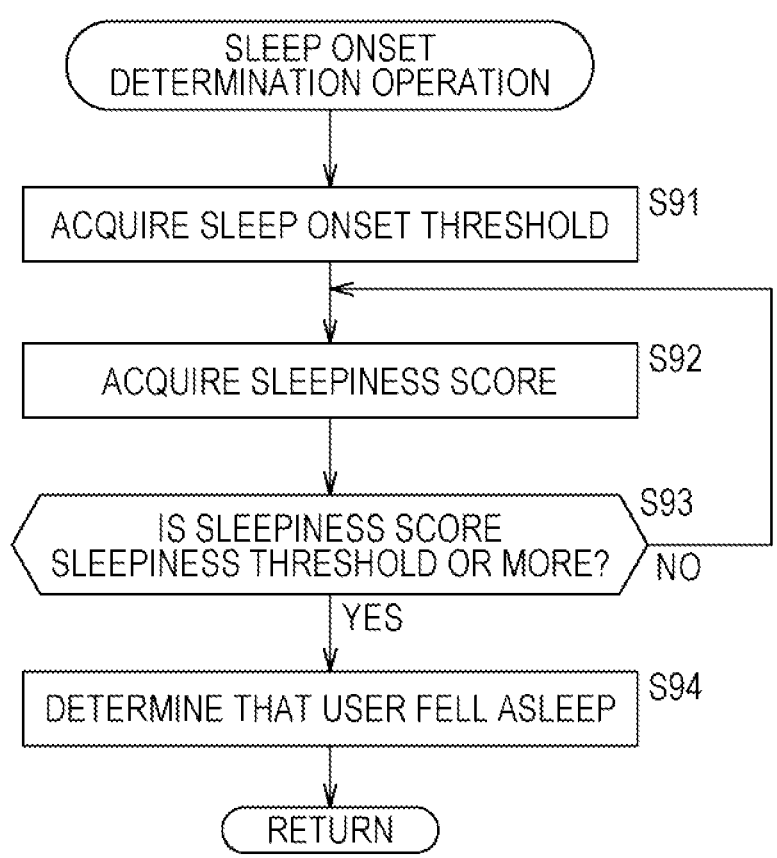
FIG. 21 is a flowchart for explaining a sleep onset determination operation.

First, the sleep onset determination unit which is an operation of detecting that the user fell asleep will be described with reference to a flowchart in FIG. 21. The sleep onset determination operation is an operation performed when it is determined that the user needs to sleep.

In step S91, the detection unit 84 acquires a sleep onset threshold. The sleep onset threshold is a sleepiness score which is a reference to detect that the user fell asleep, is calculated in advance based on the sleepiness score of the user of the information processing device 1 and sleepiness scores of a plurality of users, and is stored in the storage unit 16. When the sleepiness score of the user is higher than the sleep onset threshold, it is determined that the user fell asleep.

In step S92, the detection unit 84 acquires the sleepiness score updated in step S77 in FIG. 18.

In step S93, the detection unit 84 determines whether or not the updated sleepiness score is the sleep onset threshold or more, and, when determining that the updated sleepiness score is less than the sleep onset threshold, repeats operations subsequent to step S92.

Meanwhile, when it is determined in step S93 that the updated sleepiness score is the sleep onset threshold or more, in step S94, the detection unit 84 determines that the user fell asleep and outputs information of this determination result to the music selection unit 81 and the information management unit 83.

When it is determined in step S94 that the user fell asleep or when it is determined a predetermined number of times in step S93 that the sleepiness score is less than the sleep onset threshold, the operation returns to step S79 in FIG. 18, and subsequent operations are performed.

Figure 22:
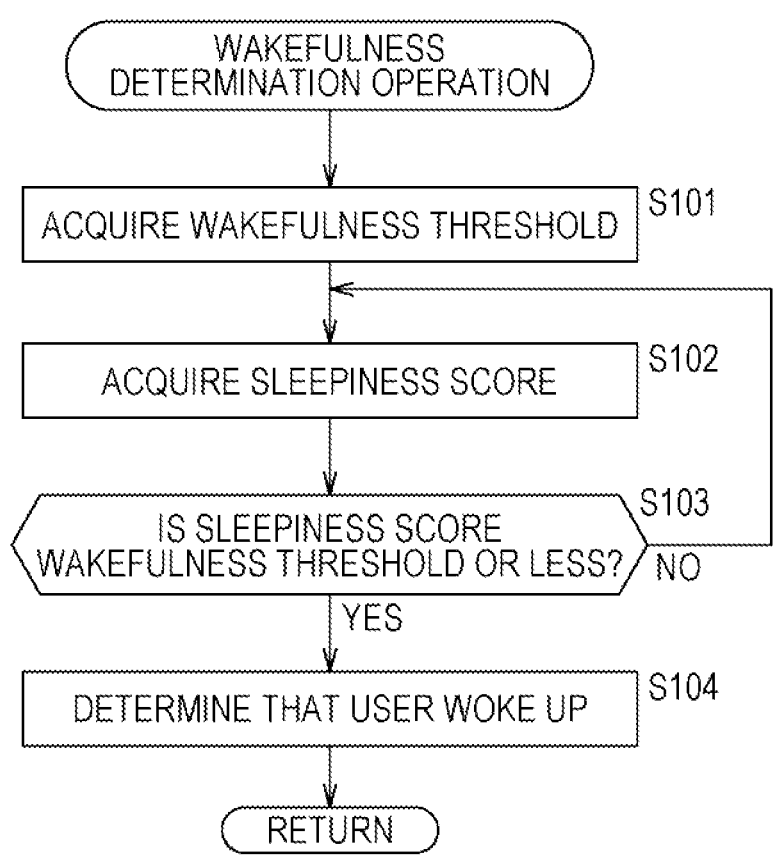
FIG. 22 is a flowchart for explaining a wakefulness determination operation.

Next, the wakefulness determination operation which is an operation of detecting that the user wakes up will be described with reference to the flowchart in FIG. 22. The wakefulness determination operation is an operation performed when it is determined that the user needs to wake up.

In step S101, the detection unit 84 acquires a wakefulness threshold. The wakefulness threshold is a sleepiness score which is a reference to detect that the user wakes up, is calculated in advance based on the sleepiness score of the user of the information processing device 1 and sleepiness scores of a plurality of users, and is stored in the storage unit 16. When the sleepiness score of the user is lower than the wakefulness threshold, it is determined that the user woke up.

In step S102, the detection unit 84 acquires the sleepiness score updated in step S77 in FIG. 18.

In step S103, the detection unit 84 determines whether or not the updated sleepiness score is the wakefulness threshold or less and, when determining that the updated sleepiness score exceeds the wakefulness threshold, repeats operations subsequent to step S102.

Meanwhile, when it is determined in step S103 that the updated sleepiness score is the wakefulness threshold or more, in step S104, the detection unit 84 determines that the user woke up and outputs information of this determination result to the music selection unit 81 and the information management unit 83.

When it is determined in step S104 that the user woke up or when it is determined a predetermined number of times in step S103 that the sleepiness score exceeds the wakefulness threshold, the operation returns to step S79 in FIG. 18, and subsequent operations are performed.

Figure 23:
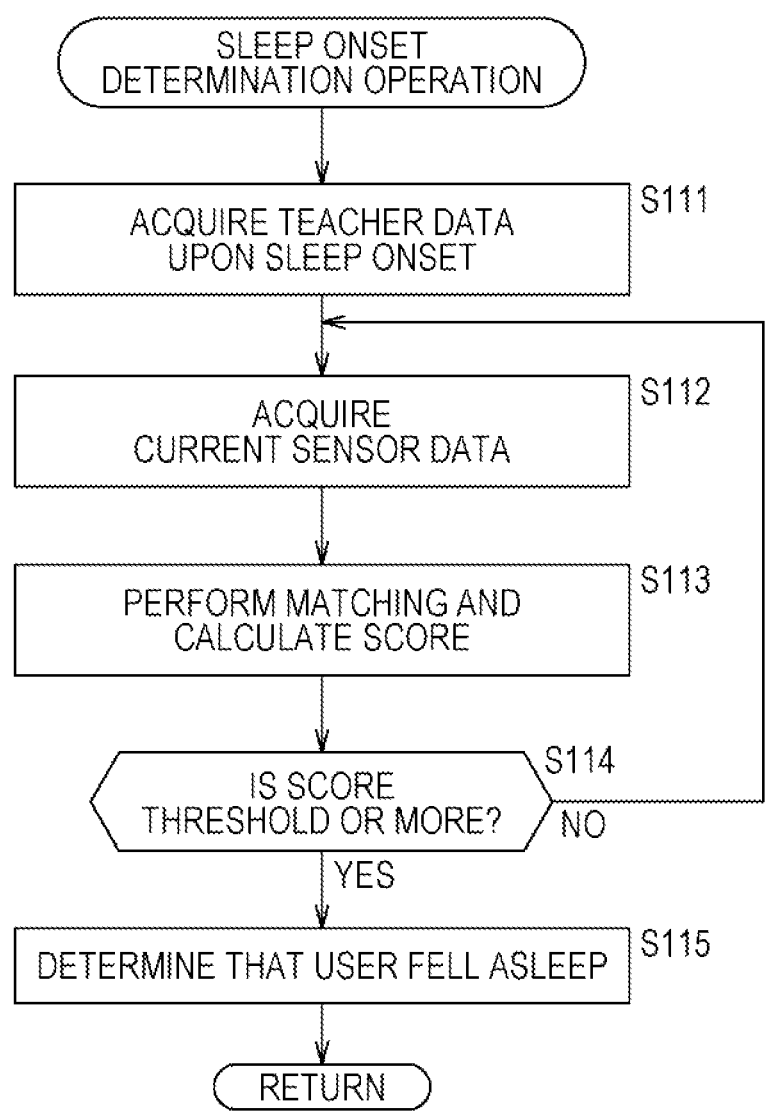
FIG. 23 is a flowchart for explaining another sleep onset determination operation.

Next, another sleep onset determination operation will be described with reference to the flowchart in FIG. 23. The operation in FIG. 23 differs from the operation in FIG. 21 in determining whether or not the user fell asleep, based on sensor data detected by the sensor unit 12.

In step S111, the detection unit 84 acquires teacher data at a time of sleep onset. The teacher data at the time of sleep onset is sensor data detected by the sensor unit 12 when the user fell asleep or data which is extracted from the sensor data and which indicates a feature of the sensor data, and is stored in the storage unit 16 in advance.

In step S112, the detection unit 84 acquires current sensor data.

In step S113, the detection unit 84 calculates a matching score by matching the acquired sensor data or the feature extracted from the sensor data, and the teacher data.

In step S114, the detection unit 84 determines whether or not the matching score is the threshold or more, and, when determining that the matching score is less than the threshold, repeats operations subsequent to step S112.

Meanwhile, when it is determined in step S114 that the matching score is the threshold or more, in step S115, the detection unit 84 determines that the user fell asleep and outputs information of this determination result to the music selection unit 81 and the information management unit 83.

When it is determined in step S115 that the user fell asleep or when it is determined a predetermined number of times in step S114 that the matching score is less than the threshold, the operation returns to step S79 in FIG. 18, and subsequent operations are performed.

Figure 24:
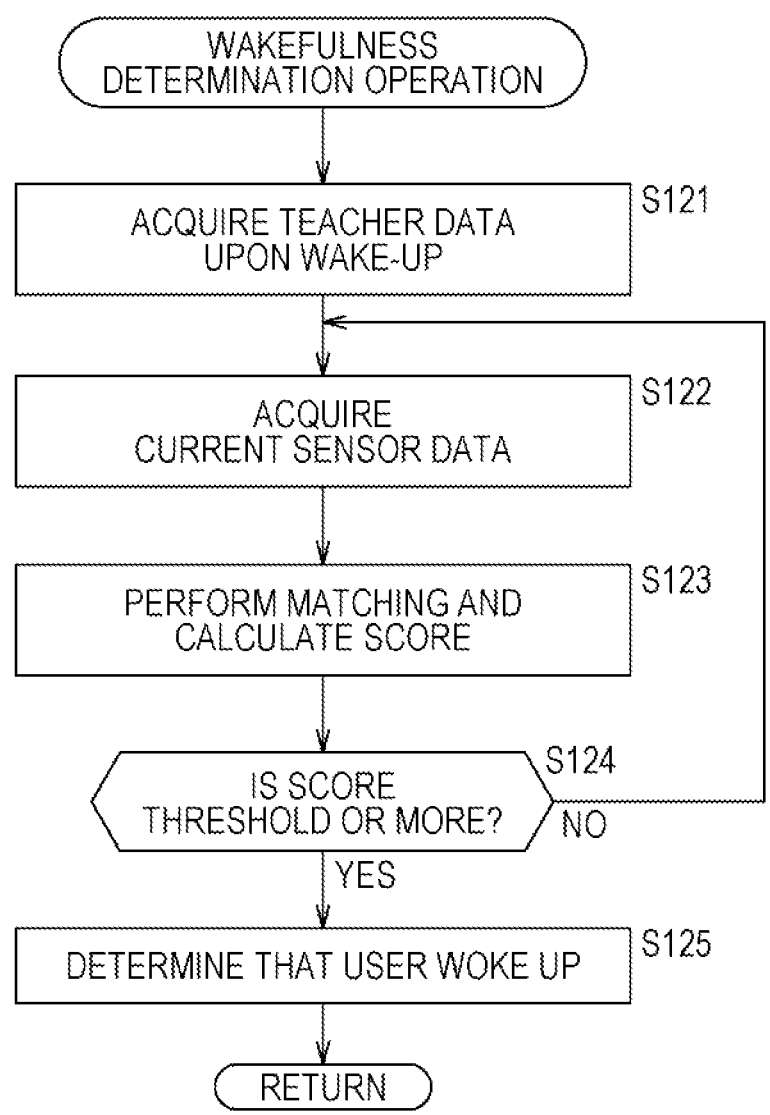
FIG. 24 is a flowchart for explaining another wakefulness determination operation.

Next, another wakefulness determination operation will be described with reference to a flowchart of FIG. 24. The operation in FIG. 24 differs from the operation in FIG. 22 in determining whether or not the user woke up, based on sensor data detected by the sensor unit 12.

In step S121, the detection unit 84 acquires teacher data upon at a time of wake-up. The teacher data at the time of wake-up is sensor data detected by the sensor unit 12 when the user woke up or data which is extracted from the sensor data and which indicates a feature of the sensor data, and is stored in the storage unit 16 in advance.

In step S122, the detection unit 84 acquires current sensor data.

In step S123, the detection unit 84 calculates a matching score by matching the acquired sensor data or the feature extracted from the sensor data, and the teacher data.

In step S124, the detection unit 84 determines whether or not the matching score is the threshold or more, and, when determining that the matching score is less than the threshold, repeats operations subsequent to step S122.

Meanwhile, when it is determined in step S124 that the matching score is the threshold or more, in step S125, the detection unit 84 determines that the user woke up and outputs information of this determination result to the music selection unit 81 and the information management unit 83.

When it is determined in step S125 that the user woke up or when it is determined a predetermined number of times in step S124 that the matching score is less than the threshold, the operation returns to step S79 in FIG. 18, and subsequent operations are performed.

According to the above series of operations, the information processing device 1 can get the user to sleep when the user needs to sleep and wake the user up when the user needs to wake up, so that it is possible to improve sleep efficiency of the user.

5. Modified Example

Although different music is selected based on a sleep onset score or a wakefulness score, and a sleepiness score and is played back above, predetermined music may be arranged according to a sleep onset score or a wakefulness score, and a sleepiness score to play back music of different atmospheres.

Figure 25:
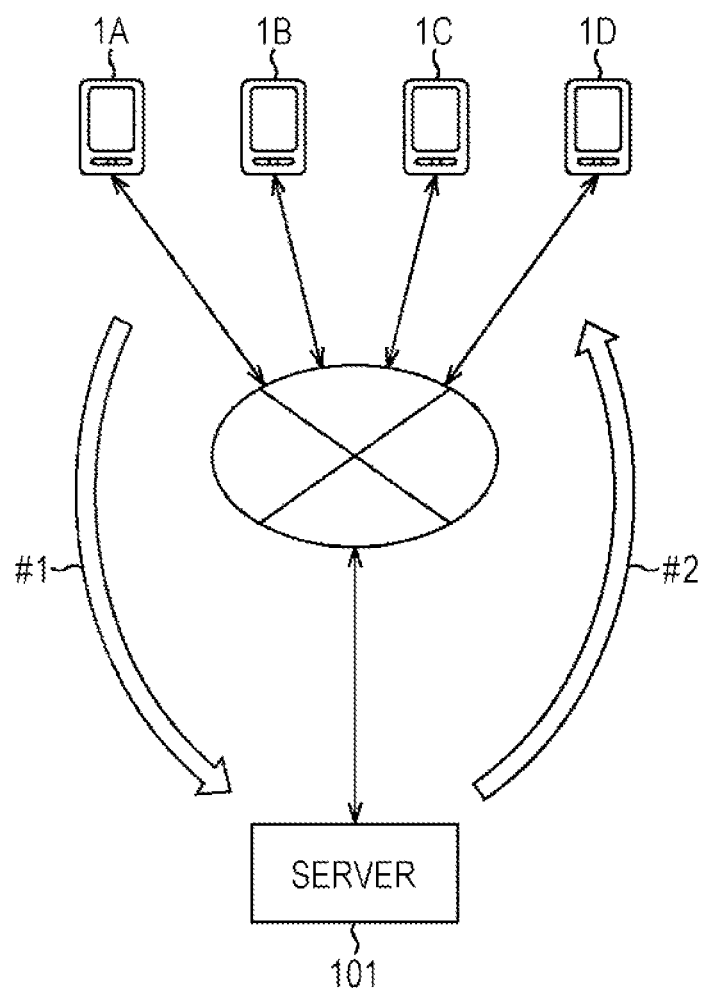
FIG. 25 is a view illustrating learning of a sleepiness determinator.

A server may perform learning instead of a sleepiness determinator which forms a sleepiness determination unit 63. FIG. 25 is a view illustrating learning of the sleepiness determinator. In an example in FIG. 25, information processing devices 1A to 1D are connected to a server 101 through a network. The information processing devices 1A to 1D employ the same configurations and the same functions as those of the above information processing device 1.

The information processing devices 1A to 1D upload sensor data detected by a sensor unit 12, to the server 101. The server 101 accumulates sensor data transmitted from the information processing devices 1A to 1D, and performs learning of the sleepiness determinator based on the sensor data transmitted from the information processing devices 1A to 1D. The server 101 transmits the data of the sleepiness determinator updated by learning, to the information processing devices 1A to 1D.

By using the updated sleepiness determinator, the information processing devices 1A to 1D can each calculate a precise sleepiness score.

Although the information processing devices 1 performs various operations including determination as to whether or not the user needs to wake up or whether or not the user needs to sleep as described above, the server 101 can also perform operations other than, for example, detection of sensor data and playback of music. In this case, configurations illustrated in FIG. 8 to FIG. 11 except a sensor data acquisition unit 61 in FIG. 10 and a playback unit 82 in FIG. 11 are adequately realized by the server 101.

Further, although the user is got to sleep or woken up by playing music, a means for getting the user to sleep or waking up the user is not limited to playing back music. The means for getting the user to sleep or waking up the user may include using a device which can be controlled by the information processing device 1 and plays back and displays video images, an air conditioner and a vibration generation device.

When, for example, the air conditioner is used as the means for getting the user to sleep or waking up the user, the information processing device 1 performs an operation of controlling the air conditioner to adjust a room temperature to an adequate temperature in order to get the user to sleep and adjust a room temperature to a temperature lower or higher than the adequate temperature in order to wake up the user.

Although whether the user needs to wake up or sleep is determined according to an action schedule of the user, and the degree of necessity of waking up is determined when it is determined that the user needs to wake up while the degree of necessity of sleeping is determined when it is determined that the user needs to sleep, it may be set to perform only one of either the former determination or the latter determination. That is, the information processing device 1 may perform only determination as to whether the user needs to wake up or sleep, and the information processing device 1 can perform only determination as to the degree of necessity of waking up when the user needs to wake up or the degree of necessity of sleeping when the user needs to sleep.

Further, instead of determining both of whether or not the user needs to wake up and whether or not the user needs to sleep, it is possible to perform only determination as to whether or not the user needs to wake up or only determination as to whether or not the user needs to sleep. When whether or not the user needs to wake up is determined, the information processing device 1 can also determine the degree of necessity of waking up. Further, when whether or not the user needs to sleep is determined, the information processing device 1 can also determine the degree of necessity of sleeping.

[Example Structure of Computer]

The above described series of operations can be performed by hardware, and can also be performed by software.

When a series of operations is executed by software, a program which configures this software is installed to a computer embedded in dedicated hardware or a general-purpose personal computer from a program recording medium.

FIG. 26 is a block diagram showing an example structure of the hardware of a computer which executes the above described series of operations in accordance with programs.

A CPU (Central Processing Unit) 151, a ROM (Read Only Memory) 152 and a RAM (Random Access Memory) 153 are mutually connected through a bus 154.

An input/output interface 155 is further connected to the bus 154. The input/output interface 155 is connected with an input unit 156 formed with a keyboard and a mouse, and an output unit 157 formed with a display and speakers. Further, the input/output interface 155 is connected with a storage unit 158 formed with a hard disk or a non-volatile memory, a communication unit 159 which is formed with a network interface and a drive 160 which drives a removable medium 161.

In the computer having the above described structure, the CPU 151 loads a program stored in the storage unit 158 into the RAM 153 through the input/output interface 155 and the bus 154, and executes the program, so that the above described series of operations are performed.

The programs executed by the CPU 151 are recorded in, for example, the removable medium 161 or provided through a wired or wireless transmission medium such as a local area network, the Internet or digital broadcasting, and are installed in the storage unit 158.

The program to be executed by the computer may be a program for carrying out processes in chronological order in accordance with the sequence described in this specification, or a program for carrying out processes in parallel or whenever necessary such as in response to a call.

It should be noted that embodiments of the present technique are not limited to the above described embodiments, and various modifications may be made to them without departing from the scope of the present technique.

Modified Example

The present technique can also employ the following configuration.

(1) An information processing device has: an acquisition unit which acquires information which indicates an action schedule of a user; and a first determination unit which performs at least one of determination as to at least one of whether or not the user needs to wake up and whether or not the user needs to sleep, and determination as to a degree of necessity of waking up when the user needs to wake up and a degree of necessity of sleeping when the user needs to sleep, according to the action schedule of the user.

(2) In the information processing device described in (1), the first determination unit calculates a first score which indicates the degree of necessity of waking up or the degree of necessity of sleeping when determining the degree of necessity of waking up or the degree of necessity of sleeping.

(3) The information processing device described in (2), further has a second determination unit which calculates a second score which indicates a degree of sleepiness of the user based on data detected by a sensor.

(4) The information processing device described in (3) further has: a selection unit which selects content to play back based on the first score and the second score; and a playback unit which plays back the content selected by the selection unit.

(5) The information processing device described in (4), further has a storage unit which stores, for a plurality of items of content, information which indicates a relationship between the content and a degree of change of sleepiness in the user who views the content, and the selection unit selects the content which causes the change of the sleepiness corresponding to a difference between the first score and the second score, based on the information stored in the storage unit.

(6) In the information processing device described in (5), the second determination unit further calculates the second score based on the data detected by the sensor after the content is played back, and the information processing device further has an update unit which updates the information which is stored in the storage unit and which indicates the degree of the change of the sleepiness caused by the content played back, based on a difference between the second score calculated before the content starts being played back and the second score calculated after the content is played back.

(7) The information processing device described in any one of (1) to (6), further has: a wake-up unit which, when the first determination unit determines that the user needs to wake up and determines the degree of necessity of waking up, wakes up the user according to the degree of necessity of waking up; and a sleep onset unit which, when the first determination unit determines that the user needs to sleep and determines the degree of necessity of sleeping, gets the user to sleep according to the degree of necessity of sleeping.

(8) An information processing method includes the steps of: acquiring information which indicates an action schedule of a user; and performing at least one of determination as to at least one of whether or not the user needs to wake up and whether or not the user needs to sleep, and determination as to a degree of necessity of waking up when the user needs to wake up and a degree of necessity of sleeping when the user needs to sleep, according to the action schedule of the user.

(9) A program causes a computer to execute processing including the steps of: acquiring information which indicates an action schedule of a user; and performing at least one of determination as to at least one of whether or not the user needs to wake up and whether or not the user needs to sleep, and determination as to a degree of necessity of waking up when the user needs to wake up and a degree of necessity of sleeping when the user needs to sleep, according to the action schedule of the user.

REFERENCE SIGNS LIST

1 Information processing device, 21 Control unit, 22 Sleep-onset/wakefulness determination unit, 23 Sleepiness determination unit, 24 Music selection/playback unit, 25 Schedule DB, 26 Music DB

The invention claimed is:

1. An information processing device, comprising:
an acquisition unit configured to acquire first information which indicates an action schedule of a user;
a first determination unit configured to:
determine at least one of whether the user needs to wake up or whether the user needs to sleep;
determine a first score based on the action schedule of the user, wherein the first score indicates at least one of a degree of necessity of waking up based on the determination that the user needs to wake up or a degree of necessity of sleeping based on the determination that the user needs to sleep;
a second determination unit configured to calculate a second score which indicates a first degree of sleepiness of the user based on sensor data detected by at least one sensor, wherein the information processing device is configured to upload the sensor data to a server;
a selection unit configured to select content of different atmospheres based on at least one of the first score and the second score, wherein the selected content changes the sleepiness of the user;
a playback unit configured to play back the selected content of the different atmospheres based on the second score; and
a detection unit configured to compare, based on the playback of the selected content and based on the change of the sleepiness of the user, the second score that indicates a second degree of the sleepiness of the user with a threshold value.

2. The information processing device according to claim 1, further comprising:
a storage unit configured to store, for a plurality of items of the selected content, second information which indicates a relationship between the selected content and a degree of the change of the sleepiness of the user who views the selected content,
wherein the change of the sleepiness is based on a first difference between the first score and the second score.

3. The information processing device according to claim 1, further comprising:
a wake-up unit configured to wake up the user based on the degree of necessity of waking up and based on the determination that the user needs to wake up; and
a sleep onset unit configured to get the user to sleep based on the degree of necessity of sleeping and based on the determination that the user needs to sleep.

4. The information processing device according to claim 1, wherein the detection unit is further configured to determine, after the playback of the selected content, that the user is asleep based on the second score that is greater than the threshold value.

5. The information processing device according to claim 2, wherein
the second determination unit is further configured to calculate the second score based on the sensor data detected by the at least one sensor after the selected content is played back, and
the information processing device further comprises an update unit configured to update the second information which is stored in the storage unit and indicate the degree of the change of the sleepiness caused by the selected content played back, wherein the degree of the change of the sleepiness is indicated based on a second difference between the second score calculated before the playback of the selected content and the second score calculated after the selected content is played back.

6. An information processing method, comprising:
in an information processing device:
acquiring, by an acquisition unit, information which indicates an action schedule of a user;
determining, by a first determination unit, at least one of whether the user needs to wake up or whether the user needs to sleep;
determining, by the first determination unit, a first score based on the action schedule of the user, wherein the first score indicates at least one of a degree of necessity of waking up based on the determination that the user needs to wake up or a degree of necessity of sleeping based on the determination that the user needs to sleep;

calculating, by a second determination unit, a second score indicating a first degree of sleepiness of the user based on sensor data detected by at least one sensor, wherein the sensor data is uploaded to a server;

selecting, by a selection unit, content of different atmospheres based on at least one of the first score and the second score, wherein the selected content changes the sleepiness of the user;

playing back the selected content of the different atmospheres based on the second score; and comparing, by a detection unit, based on the playback of the selected content and based on the change of the sleepiness of the user, the second score indicating a second degree of the sleepiness of the user with a threshold value.

7. A non-transitory computer-readable medium having stored thereon, computer-executable instructions that, when executed by a processor, cause the processor to execute operations, the operations comprising:

acquiring, by an acquisition unit, information which indicates an action schedule of a user;

determining, by a first determination unit, at least one of whether the user needs to wake up or whether the user needs to sleep;

determining, by the first determination unit, a first score based on the action schedule of the user, wherein the first score indicates at least one of a degree of necessity of waking up based on the determination that the user needs to wake up or a degree of necessity of sleeping based on the determination that the user needs to sleep;

calculating, by a second determination unit, a second score indicating a first degree of sleepiness of the user based on sensor data detected by at least one sensor, wherein the sensor data is uploaded to a server;

selecting, by a selection unit, content of different atmospheres based on at least one of the first score and the second score, wherein the selected content changes the sleepiness of the user;

playing back the selected content of the different atmospheres based on the second score; and comparing, by a detection unit, based on the playback of the selected content and based on the change of the sleepiness of the user, the second score indicating a second degree of the sleepiness of the user with a threshold value.

* * * * *